(12) United States Patent
Shukla et al.

(10) Patent No.: US 11,957,690 B2
(45) Date of Patent: Apr. 16, 2024

(54) CHROMOGENIC BETA-LACTAMASE SUBSTRATE

(71) Applicant: BROWN UNIVERSITY, Providence, RI (US)

(72) Inventors: Anita Shukla, Providence, RI (US); Dahlia Alkekhia, Providence, RI (US); Shashank Shukla, Billerica, MA (US); Hannah Safford, Philadelphia, PA (US)

(73) Assignee: BROWN UNIVERSITY, Providence, RI (US)

( * ) Notice: Subject to any disclaimer, the term of this patent is extended or adjusted under 35 U.S.C. 154(b) by 0 days.

(21) Appl. No.: 17/260,894

(22) PCT Filed: Jul. 15, 2019

(86) PCT No.: PCT/US2019/041884
§ 371 (c)(1),
(2) Date: Jan. 15, 2021

(87) PCT Pub. No.: WO2020/018462
PCT Pub. Date: Jan. 23, 2020

(65) Prior Publication Data
US 2021/0252010 A1   Aug. 19, 2021

Related U.S. Application Data

(60) Provisional application No. 62/698,695, filed on Jul. 16, 2018.

(51) Int. Cl.
| | | |
|---|---|---|
| A61K 31/545 | (2006.01) | |
| A61K 47/54 | (2017.01) | |
| A61K 47/60 | (2017.01) | |
| A61K 47/61 | (2017.01) | |
| A61K 47/69 | (2017.01) | |
| A61P 31/04 | (2006.01) | |
| A61K 31/546 | (2006.01) | |

(52) U.S. Cl.
CPC .......... *A61K 31/545* (2013.01); *A61K 47/545* (2017.08); *A61K 47/60* (2017.08); *A61K 47/61* (2017.08); *A61K 47/6903* (2017.08); *A61P 31/04* (2018.01); *A61K 31/546* (2013.01)

(58) Field of Classification Search
CPC ...... A61K 47/61; A61K 47/60; A61K 31/545; A61K 31/546
See application file for complete search history.

(56) References Cited

U.S. PATENT DOCUMENTS

| | | | |
|---|---|---|---|
| 4,535,156 A | 8/1985 | Blumbach et al. | |
| 4,883,868 A | 11/1989 | Nakagawa et al. | |
| 5,233,035 A | 8/1993 | Hara et al. | |
| 7,323,303 B2 | 1/2008 | Wong et al. | |
| 7,396,926 B2 | 7/2008 | Tsien et al. | |
| 7,632,657 B2 | 12/2009 | Rambach et al. | |
| 8,092,784 B2 | 1/2012 | Mao et al. | |
| 8,097,434 B2 | 1/2012 | Yang-Woytowitz et al. | |
| 8,389,234 B2 | 3/2013 | Yang-Woytowitz et al. | |
| 8,586,325 B2 | 11/2013 | Mao et al. | |
| 8,778,627 B2 | 7/2014 | Mao et al. | |
| 8,802,387 B2 | 8/2014 | Xing et al. | |
| 8,883,772 B2 | 11/2014 | Sutton et al. | |
| 9,012,167 B2 | 4/2015 | Dallenne et al. | |
| 9,085,794 B2 | 7/2015 | Yang-Woytowitz et al. | |
| 9,138,490 B2 | 9/2015 | Cirillo et al. | |
| 9,441,261 B2 | 9/2016 | Cirillo et al. | |
| 9,453,032 B2 | 9/2016 | Sutton et al. | |
| 9,476,087 B2 | 10/2016 | Xing et al. | |
| 9,670,476 B2 | 6/2017 | Mao et al. | |
| 9,677,112 B2 | 6/2017 | Rao et al. | |
| 9,689,021 B2 | 6/2017 | Brans et al. | |
| 9,809,605 B1 | 11/2017 | Sutton et al. | |
| 9,828,622 B2 | 11/2017 | Hasan et al. | |
| 9,834,681 B2 | 12/2017 | Rao et al. | |
| 9,862,729 B2 | 1/2018 | Sutton et al. | |
| 9,902,989 B2 | 2/2018 | Yang-Woytowitz et al. | |
| 10,000,491 B2 | 6/2018 | Abe et al. | |
| 10,000,492 B2 | 6/2018 | Abe et al. | |
| 10,000,509 B2 | 6/2018 | Sutton et al. | |
| 10,041,105 B2 | 8/2018 | Li | |
| 10,175,239 B2 | 1/2019 | Cirillo et al. | |
| 2014/0219917 A1* | 8/2014 | Murthy | A61K 31/496 424/1.73 |
| 2014/0349886 A1 | 11/2014 | Lee et al. | |
| 2016/0333027 A1 | 11/2016 | Rao et al. | |
| 2016/0376629 A1 | 12/2016 | Cirillo et al. | |

(Continued)

FOREIGN PATENT DOCUMENTS

| | | | |
|---|---|---|---|
| EP | 0034759 B1 | 1/1986 | |
| EP | 0745390 A2 * | 12/1996 | ............. A61P 35/00 |
| EP | 2285381 B1 | 12/2015 | |

OTHER PUBLICATIONS

Antibiotic / Antimicrobial Resistance. (Sep. 19, 2017). Retrieved Jan. 15, 2018, from https://www.cdc.gov/drugresistance/about.html.
Bebrone, C., et al., "CENTA as a chromogenic substrate for studying β-lactamases.", Antimicrob Agents Chemother. 2001;45(6):1868-1871.
Bernabeau S. et al., "Evaluation of the β-CARBA(tm) test, a colorimetric test for the rapid detection of carbapenemase activity in Gram-negative bacilli", Journal of Antimicrobial Chemotherapy, vol. 72, Issue 6, Jun. 2017, pp. 1646-1658.
Hanaki, H. et al., "Characterization of HMRZ-86: a novel chromogenic cephalosporin for the detection of extended-spectrum β-lacatamases,", Journal of Antimicrobial Chemotherapy, vol. 53, Issue 5, May 2004, pp. 888-889.
Janaki, H., et al., "The Synthesis of 7-Substituted-3-dinitrostyryl Cephalosporins and Their Ability for Detecting Extended Spectrum β-Lactamases (ESBLs).", The Journal of Antibiotics, 58, 69.

(Continued)

*Primary Examiner* — James W Rogers
(74) *Attorney, Agent, or Firm* — Adler Pollock & Sheehan P.C.

(57) ABSTRACT

The invention provides a chromogenic β-lactam molecule that retains its diagnostic color change response when modified for conjugation to another molecule.

3 Claims, 9 Drawing Sheets

(56) References Cited

U.S. PATENT DOCUMENTS

| | | | |
|---|---|---|---|
| 2018/0094139 A1 | 4/2018 | Rao et al. |
| 2018/0094292 A1 | 4/2018 | Hasan et al. |
| 2018/0105862 A1 | 4/2018 | Dequaire-Rochelet et al. |
| 2018/0156796 A1 | 6/2018 | Geisberg |
| 2018/0282778 A1 | 10/2018 | Nordmann et al. |
| 2018/0334701 A1 | 11/2018 | Yang-Woytowitz et al. |
| 2019/0101538 A1 | 4/2019 | Cirillo et al. |

OTHER PUBLICATIONS

Jones, R. N., Wilson, H. W., Novick, W. J., Barry, A. L., & Thornsberry, C. (1982). In vitro evaluation of CENTA, a new beta-lactamase-susceptible chromogenic cephalosporin reagent. Journal of Clinical Microbiology, 15(5), 954-958.

Khan, et al., "Rapid optical determination of β-lactamase and antibiotic activity,", BMC Microbiol., 2014, 14:84.

Korobova, A.G., et al., "The Application of Selective Chromogenic Agar for Detecting Enterobacteria with Production of Beta-Lactamases", 2015.

Livermore, D.M., et al., "Evaluation of the chromogenic Cica-β-Test for detecting extended-spectrum, AmpC and metallo-β-lactamases", Journal of Antimicrobial Chemotherapy, vol. 60, Issue 6, Dec. 2007, pp. 1375-1379.

Morandi, F., et al., "Nanomolar inhibitors of AmpC β-lactamase.", J. Am. Chem. Soc., 2003, 125(3), 685-695.

Mura, T., et al., "Development of a novel chromogenic method, Penta-well test, for rapid prediction of β-lactamase classes provided in clinical Enterobacteriaceae isolates.", Diagnostic Microbiology and Infectious Disease, 83(1), 25-29.

Page, M. I. & Proctor, P. (1984). Mechanism of β-lactam Ring Opening in Cephalosporins. Journal of the American Chemical Society, 106(13), 3820-3825.

PCTUS2019041884, "International Search Report and Written Opinion", dated Nov. 15, 2019, 10 Pages.

Shaikh, S., Fatima, J., Shakil, S., Rizvi, S. M. D., & Kamal, M. A. (2015). Antibiotic resistance and extended spectrum beta-lactamases: Types, epidemiology and treatment. Saudi Journal of Biological Sciences, 22(1), 90-101. http://doi.org/10.1016/j.sjbs.2014.08.002.

Shao, et al., "Enzyme responsive luminescent ruthenium(II) cephalosporin probe for intracellular imaging and photoinactivation of antibiotics resistant bacteria", Chem. Commun., 2012, 48, 1739-1741.

Simner, PJ, et al., "Carbapenesmase Detection among Carbapenem-Resistant Glucose-Nonfermenting Gram-Negative Bacilli.", J Clin Microbiol 2017;55(9):2858-2864.

Van Berkel, et al., "Assay platform for clinically relevant metallo-β-lactamases,", J. Med. Chem., 56, 6945-6953 (2013).

Ventola, C. L. (2015). The Antibiotic Resistance Crisis: Part 1: Causes and Threats. Pharmacy and Therapeutics, 40(4), 277-283.

Vrioni, G., et al., "Performance of the βLACTA(tm) test for rapid detection of expanded-spectrum cephalosporin-non-susceptible Enterobacteriaceae.", Journal of Global Antimicrobial Resistance, 10, 285-288. https://doi.org/https://doi.org/10.1016/j.jgar.2017.05.018.

Wassef, Mona A., et al., "Chromgenic Cica-β Testing for Detection of Extended-Spectrum and AmpC β-Lactamases Among Cefoxitin-Resistant Isolates", Laboratory Medicine, vol. 44, Issue 1, Feb. 2013, pp. 25-28.

Kiao et al., "Novel fluorescent cephalosporins," Eur. J. Med. Chem. (Nov. 2012).

Xin et al., "Identification of a Monoacid-Based, Cell Permeable, Selective Inhibitor of Protein Tyrosine Phosphatase 1B," Bioorganic & Medicinal Chemistry Letters 13 (2003) 3947-3950.

Yu, S., Vosbeek, A., Corbella, K., Severson, J., Schesser, J., & Sutton, L. D. (2012). A chromogenic cephalosporin for β-lactamase inhibitor screening assays. Analytical Biochemistry, 428(2), 96-98.

Yu, F. et al. (2018), Site-Specific Photoconjugation of Beta-Lactamase Fragments to Monoclonal Antibodies Enables Sensitive Analyte Detection via Split-Enzyme Complementation. Biotechnol. J., 13:1700688.

\* cited by examiner

CHROMOGENIC BETA-LACTAMASE SUBSTRATE

REFERENCE TO RELATED APPLICATIONS

This application is a national phase filing under 35 U.S.C. § 371 of International Application No. PCT/US2019/041884 filed Jul. 15, 2019, which claims priority to U.S. Ser. No. 62/698,695, filed Jul. 16, 2018, the entire contents of which are hereby incorporated by reference herein.

STATEMENT REGARDING FEDERALLY SPONSORED RESEARCH

This invention was made with government support under grant no. N00014-17-2120 awarded by the Office of Naval Research. The government has certain rights in the invention.

FIELD OF THE INVENTION

This invention generally relates to assays, e.g., enzyme assays, involving penicillins or cephalosporins.

BACKGROUND OF THE INVENTION

Antibiotic-resistant bacteria, such as methicillin-resistant *Staphylococcus aureus* (MRSA), are serious medical threats. See, Ventola, Pharmacy and Therapeutics, 40(4), 277-283 (April 2015). See also, Tognetti et al., J. Eur. Acad. Dermatol. Venereol. 26 (8), 931-941 (August 2012). The U.S. Centers for Disease Control estimated these bacteria cause over two million illnesses and 23,000 deaths annually in the United States alone, partly because of incorrect prescriptions and administrations of antibiotics. See, Biggest Threats and Data—Antibiotic/Antimicrobial Resistance (retrieved from cdc.gov on Jun. 8, 2019). Rapid detection of antibiotic-resistant bacteria enables the rapid treatment of these infections.

β-lactamases (βLs) are bacterially-produced enzymes that hydrolyze the four-membered β-lactam ring present in several antibiotics, including penicillins and cephalosporins, inactivating the antibiotic and facilitating antibiotic resistance. See, Shaikh et al., Saudi J. Biol. Sci., 22(1), 90-101 (January 2015) and Livermore & Brown, J. Antimicrob. Chemother. 48 Suppl. 1, 59-64 (2001). The carboxylic acid group on the β-lactamase substrates is the β-lactamase enzyme recognition site. See, Morandi et al. J. Am. Chem. Soc., 125(3), 685-695 (2003). Thus, proper detection of β-lactamase-producing bacteria is important for optimizing treatment.

Several chromogenic β-lactamase molecules have been diagnostic markers of β-lactamase production, including CENTA, nitrocefin, and PADAC. See, Jones et al., J. Clin. Microbiol. 15(5), 954-958 (May 1982). These chromogenic β-lactamase molecules undergo a color change in the presence of β-lactamases when their β-lactam rings are enzymatically cleaved, and the subsequent electron transfer results in a structural change. See, Page & Proctor, J. Am. Chem. Soc., 106(13), 3820-3825 (1984).

To effectively treat and eradicate infections, the medical field needs precise and facile detection of the presence of antibiotic-resistant bacteria in wounds. Current methods are limited in providing a clear visual readout with no additional equipment or expertise. There remains a need in the art for other chromogenic β-lactamase molecules.

SUMMARY OF THE INVENTION

The inventors observed that chemical modification of commercially available chromogenic β-lactamase substrates (e.g., CENTA) leads to a loss in β-lactamase-responsive color change because the carboxylic acid group on the β-lactamase substrates is the bacterial enzymes' recognition site and must be protected from chemical modification. By contrast, the invention provides a chromogenic β-lactam molecule (substrate) that retains its diagnostic color change response when modified for conjugation to another molecule. The invention provides a β-lactamase substrate with a chromophore leaving group at one end, and an easily modifiable group (e.g., amine, carboxylic acid, or maleimide) at another end, which can be conjugated to polymers while the carboxylic group β-lactamase recognition site remains protected during the reactions. The invention provides a chromogenic β-lactamase substrate that can be covalently attached to polymers and changes color in the presence of β-lactamases and β-lactamase producing bacteria. The inventors have successfully conjugated a β-lactamase substrate to polymers to form hydrogels that changed color in response to β-lactamase.

In a first embodiment, the invention provides a β-lactam molecule, where the molecule comprises:
 (a) a β-lactam ring
 (b) a primary amine; and
 (c) a 4-nitrobenzenethiol leaving group.

In a second embodiment, the molecule has the chemical formula selected from the group consisting of:

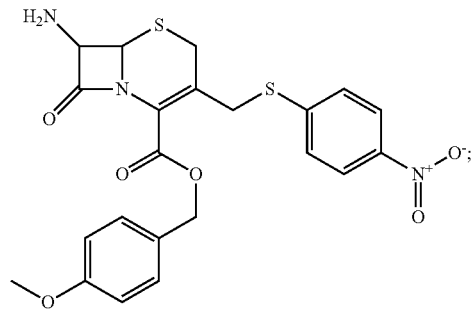

(Protected ANT)

Compound 1

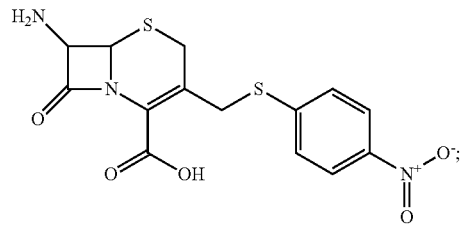

(ANT)

Substrate Compound 2

-continued

Compound 3

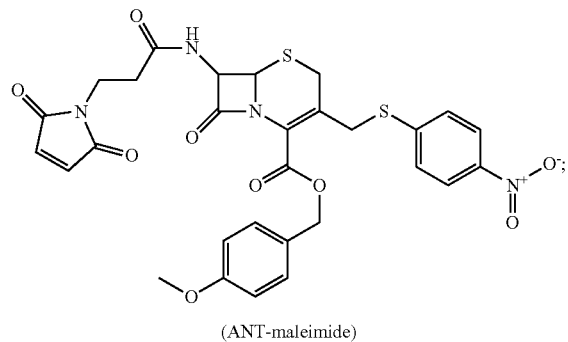

(ANT-maleimide)
3

Conjugated Compound 4

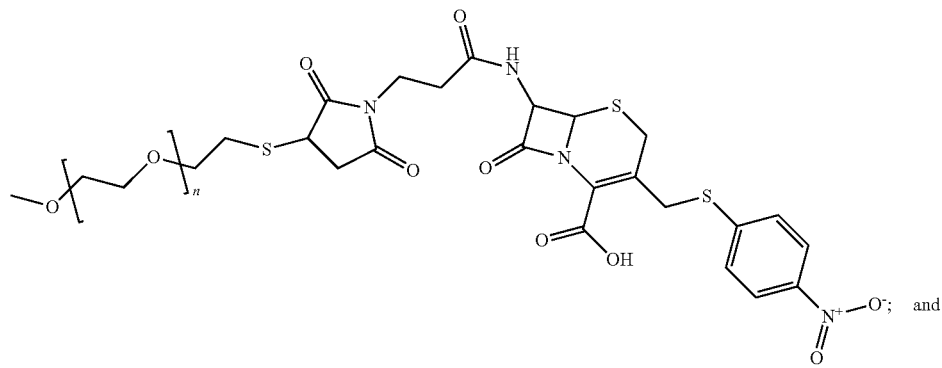

4

Conjugated Compound 5

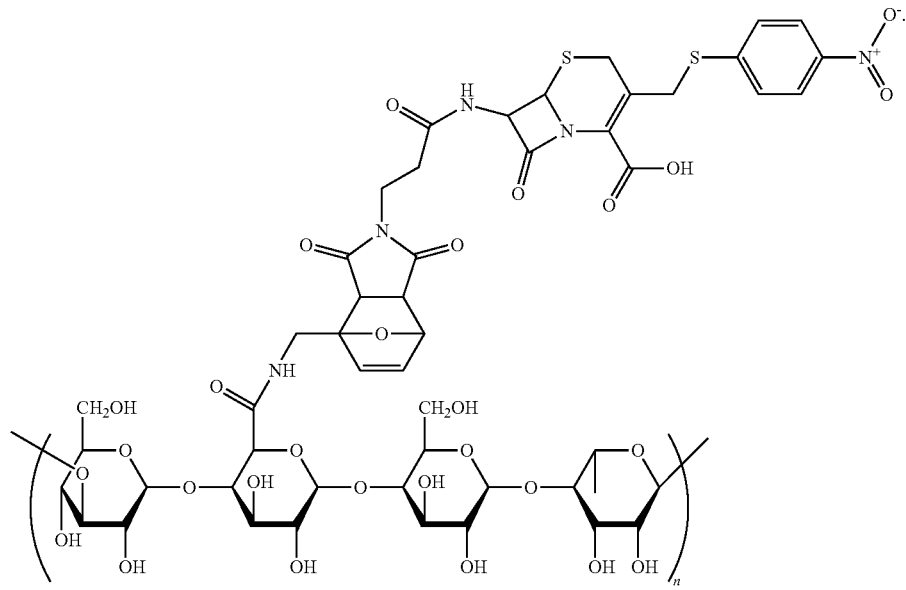

The β-lactamase Substrate Compound 2 and β-lactamase substrate Conjugated Compound 4 can be hydrolyzed by a range of β-lactamases at a kinetic rate similar to commercially available chromogenic β-lactamase substrates. These substrates show a color change from clear to yellow in the presence of β-lactamases and β-lactamase-producing bacteria, even after conjugation to polymers with Conjugated Compound 4. Kinetic analysis demonstrated the β-lactamase substrate response to various types of β-lactamases from different bacterial species.

The β-lactam molecules Compound 1 and Substrate Compound 2 contain a primary amine on the β-lactam ring that allows those of ordinary skill in the chemical art to conjugate the β-lactam molecule to other molecules without losing responsiveness to β-lactamase substrates. In a third embodiment, wherein the β-lactam molecule is conjugated to another molecule. See, e.g., Conjugated Compound 4. In a fourth embodiment, the molecule is conjugated to a macromolecule. See, Conjugated Compound 4. In a fifth embodiment, the β-lactam molecule is conjugated to a macromolecule selected from the group consisting of gellan, polyethylene glycol (PEG), hyaluronic acid and alginate. Thus, the chromogenic β-lactamase substrate can be conjugated to various polymers for developing biomaterials with β-lactamase detection functionality. In a sixth embodiment, the invention provides formulated hydrogels, which incorporate the substrate covalently attached to the polymer backbone, that changed color in the presence of β-lactamases demonstrating the potential of our approach to developing diagnostic biomaterial. A definite color change of the hydrogels occurs when exposed to the β-lactamase enzyme, indicating potential future use in infections, and the versatility of the inventive approach.

In a seventh embodiment, the invention provides a formulation comprising a β-lactam molecule, where the molecule comprises:

(a) a β-lactam ring
(b) a primary amine; and
(c) a 4-nitrobenzenethiol leaving group.

In an eighth embodiment, the formulation comprises a molecule having a chemical formula selected from the group consisting of:

Compound 1

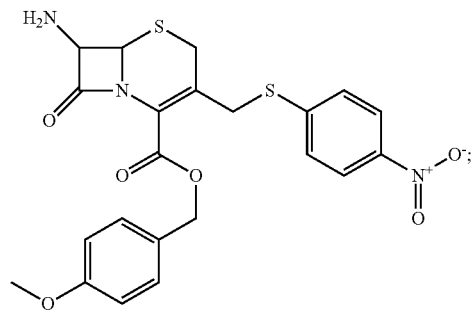

(ANT-maleimide)

Substrate Compound 2

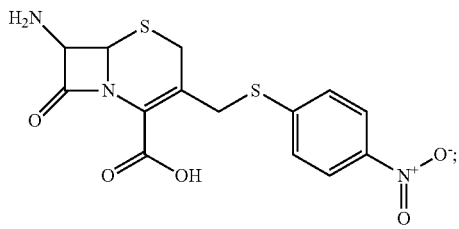

Compound 3

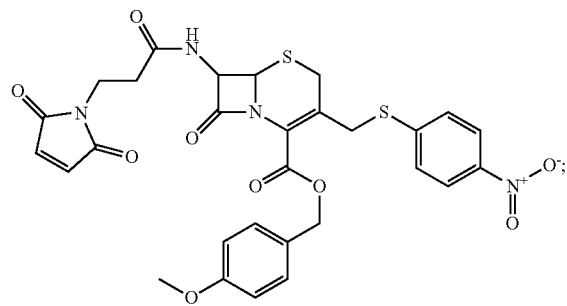

3

Conjugated Compound 4

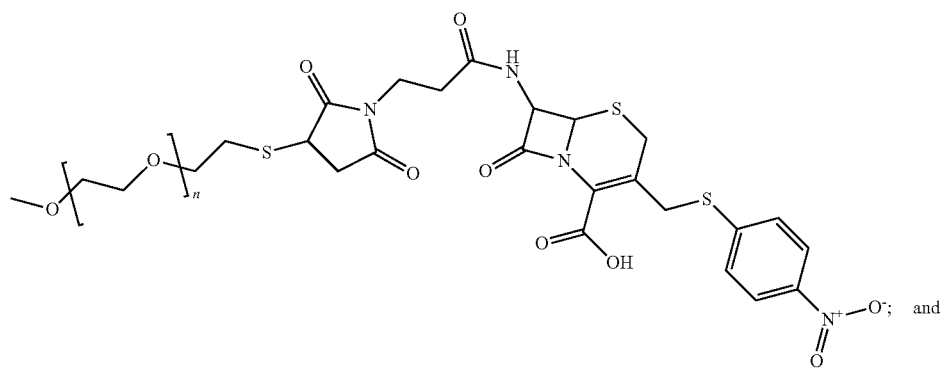

and

4

-continued

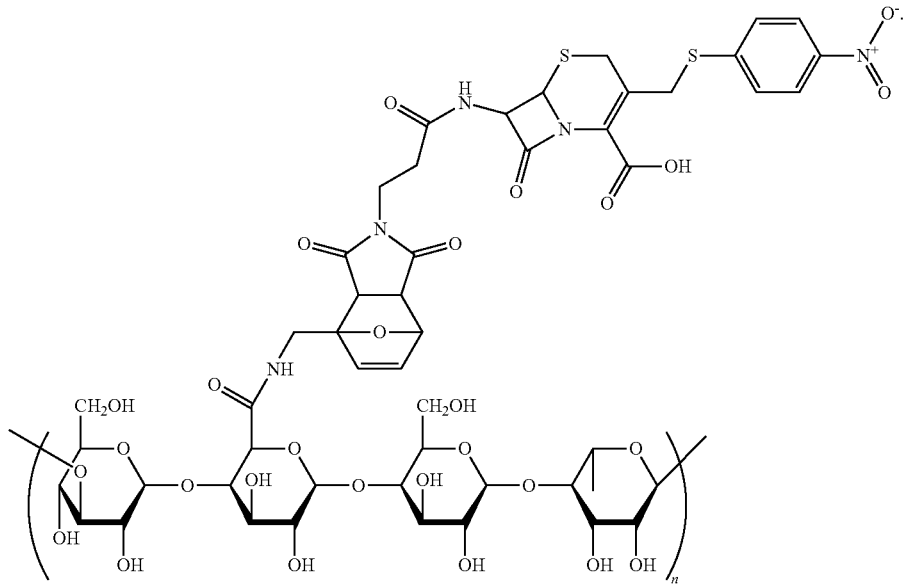

Conjugated Compound 5

In a ninth embodiment, the formulation is a wound dressing hydrogel.

In a tenth embodiment, the invention provides a method of synthesizing a molecule having the chemical formula:

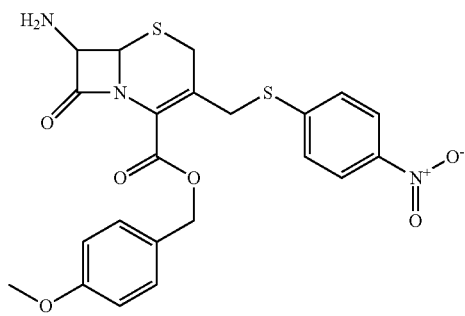 [SMILES: COc1ccc(COC(=O)C2=C(CSc3ccc([N+](=O)[O-])cc3)CSC3C(N)C(=O)N23)cc1]

The method comprises the step of combining 7-amino-3-chloromethyl-3-cephem-4-carboxylic acid p-methoxybenzyl ester hydrochloride (ACLE) with 4-nitrobenzenethiol (NBT) in the presence of triethylamine and 4-methylmorpholine (NMM). See, the synthesis scheme of FIG. 1 or FIG. 11.

In an eleventh embodiment, the method further comprises the step of performing liquid chromatography/mass spectroscopy (LC-MS) analysis on the product. The results of the LC-MS analysis indicates the synthesis of Compound 1.

In a twelfth embodiment, the invention provides a method of synthesizing a molecule having the chemical formula:

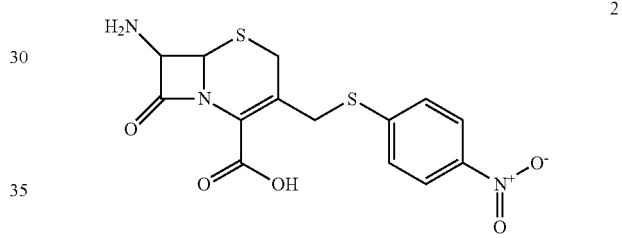

The deprotection method comprises the steps of (a) incubating Compound 1 with maleimide in dichloromethane, (b) adding anisole, (c) adding trifluoroacetic acid, and (d) incubating on ice. See, the synthesis scheme of FIG. 8 and FIG. 11.

In a thirteenth embodiment, the method further comprises the step of performing nuclear magnetic resonance analysis on the product. The results of the NMR analysis indicates the synthesis of Substrate Compound 2.

In a fourteenth embodiment, the invention provides a method of synthesizing a molecule having the chemical formula:

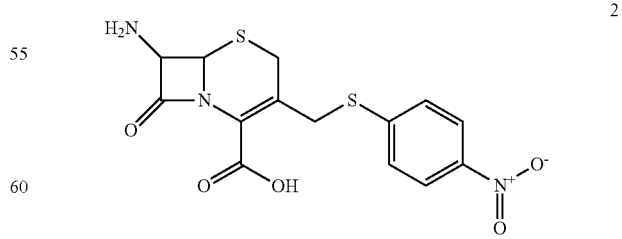

The synthetic method comprises the steps of combining ACLE with NBT in the presence of triethylamine and NMM, then (a) incubating the resulting Compound 1 with maleimide in dichloromethane, (b) adding anisole, (c) adding trifluoroacetic acid, and (d) incubating on ice. See, the synthesis scheme of FIG. 8 and FIG. 11.

In a fifteenth embodiment, the invention provides a method of synthesizing a molecule having the chemical formula:

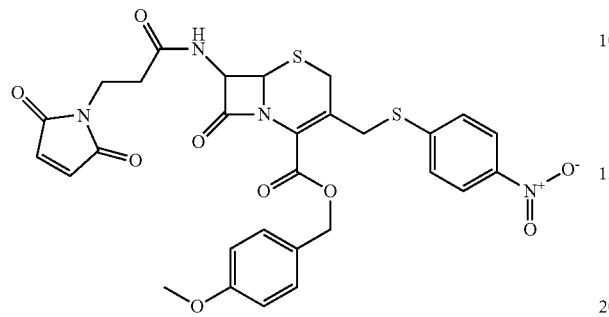

3

The method comprises the steps of (a) adding Compound 1 to maleimide, (b) dissolving the combination of step (a) in dimethylformamide; and (c) adding hexafluorophosphate azabenzotriazole tetramethyl uronium (HATU). See, the synthesis scheme of FIG. 8 and FIG. 12.

In a sixteenth embodiment, the method further comprises the step of performing nuclear magnetic resonance analysis on the product. The results of the NMR analysis indicates the synthesis of Compound 3.

In a seventeenth embodiment, the invention provides a method of synthesizing a molecule having the chemical formula:

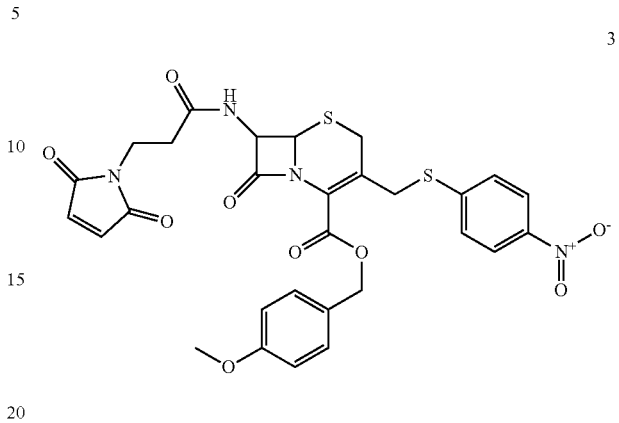

3

The synthetic method comprises the steps of combining ACLE with NBT in the presence of triethylamine and NMM, then (a) adding Compound 1 to maleimide; (b) dissolving the combination of step (a) in dimethylformamide; and (c) adding hexafluorophosphate azabenzotriazole tetramethyl uronium (HATU). See, the synthesis scheme of FIG. 8.

In an eighteenth embodiment, the invention provides a method of synthesizing a molecule having the chemical formula:

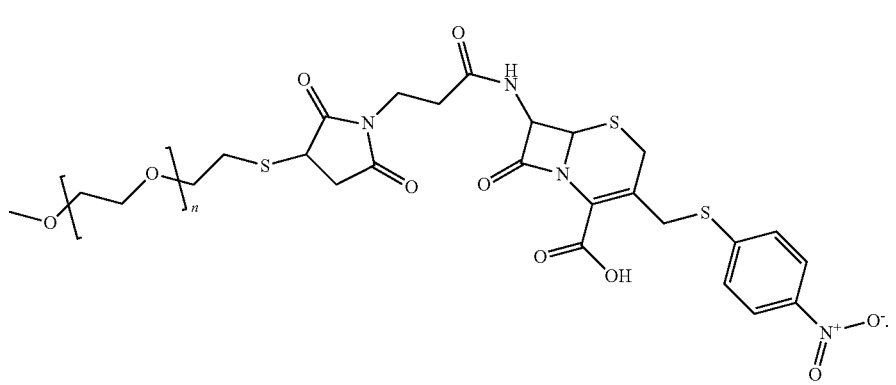

4

The method comprises the step of conjugating Compound 3 was conjugated to macromolecule by a Michael-type addition.

In a nineteenth embodiment, the method further comprises the step of performing nuclear magnetic resonance analysis on the product. The results of the NMR analysis indicates the synthesis of Conjugated Compound 4. See, the synthesis scheme of FIG. 8 and FIG. 13.

In a twentieth embodiment, the invention provides a method of synthesizing a molecule having the chemical formula:

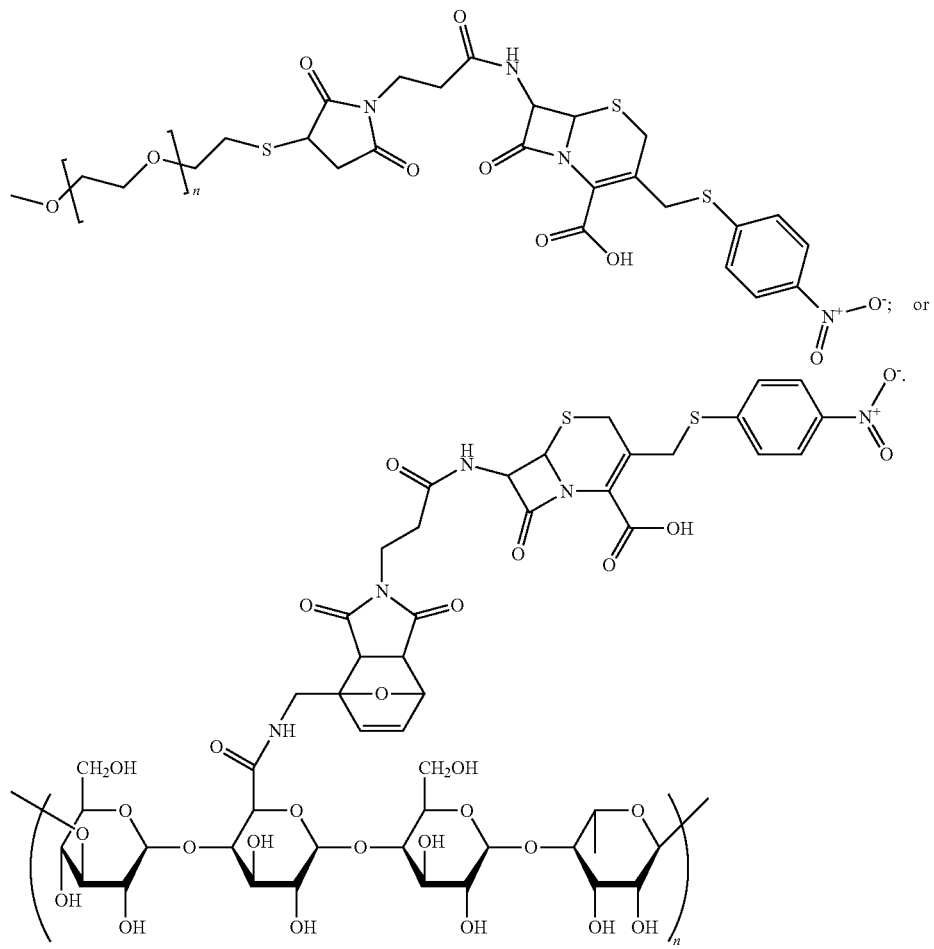

The synthetic method comprises the steps of combining ACLE with NBT in the presence of triethylamine NMM, then (a) adding Compound 1 to maleimide; (b) dissolving the combination of step (a) in dimethylformamide; and (c) adding hexafluorophosphate azabenzotriazole tetramethyl uronium (HATU), and then conjugating Compound 3 to a macromolecule by a Michael-type addition. See, the synthesis scheme of FIG. 8.

In a twenty-first embodiment, the invention provides a method for measuring the cleavage by a β-lactamase of a molecule containing a β-lactam ring, a primary amine, and a 4-nitrobenzenethiol leaving group. The method comprises the steps of:

(1) providing a sample of the molecule in a buffer;

(2) measuring the color of the sample of the molecule;

(3) adding a β-lactamase to the sample of the molecule;

(4) measuring the color change to the sample of the molecule following the addition of the β-lactamase.

A color change indicates the cleavage of the β-lactam ring in the molecule.

In a twenty-second embodiment, the molecule has the chemical formula:

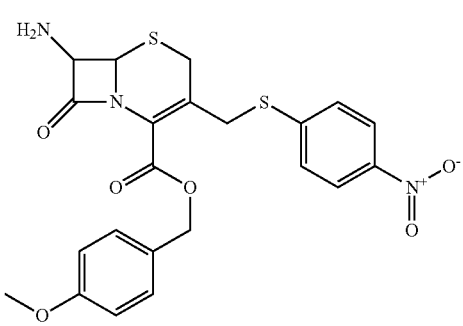 [SMILES: COc1ccc(COC(=O)C2=C(CSc3ccc([N+](=O)[O-])cc3)CSC3C(N)C(=O)N23)cc1]

In a twenty-third embodiment, the color change measured is a decrease in the peak at 260 nm. See, FIG. 2. In a twenty-fourth embodiment, the color change comes with a shift in the molecule's absorbance spectrum upon adding the β-lactamase. See, FIG. 3. See also, Page & Proctor, J. Am. Chem. Soc., 106(13), 3820-3825 (1984). In a sixteenth, the shift in the absorbance spectrum is a shift in the maximum absorbance peak shifts from 345 nm to 410 nm.

In a twenty-fifth embodiment, the method for measuring the cleavage by a β-lactamase further comprises the steps of (1) providing a second sample of the molecule in a buffer, wherein the second sample is a control sample; and (2) measuring color of the second sample; wherein a color change in the β-lactamase sample relative to the color of the second sample indicates the cleavage of the β-lactam ring in the molecule in the β-lactamase sample. In a twenty-sixth embodiment, the β-lactamase is a penicillinase or a cephalosporinase. In a twenty-seventh embodiment, the β-lactamase is an extended-spectrum β-lactamases (ESBL) or a metallo-β-lactamase.

BRIEF DESCRIPTION OF THE DRAWINGS

FIG. 3 is a set of absorbance spectrum charts showing the color change of Compound 1 (ANT) in the presence of a β-lactamase came with a definite shift in Compound 1 (ANT) absorbance spectrum upon adding penicillinase, thus cleaving the β-lactam ring and expelling the 3'-leaving group.

FIG. 16 is a spectral scan chart of Conjugated Compound 4 after incubation in phosphate-buffered saline or β-lactamase from Bacillus cereus.

FIG. 17 shows the β-lactamase substrate-gellan synthesis scheme. A color change occurs when 2% w/v hydrogels exposed to 1× phosphate-buffered saline and 400 U/mL penicillinase.

FIG. 18 is an absorbance spectrum graph showing the response of Substrate Compound 2 incubated with 50 U/mL from β-lactamases from Pseudomonas aeruginosa (with 10% dimethyl sulfoxide) after ninety minutes.

FIG. 19 is an absorbance spectrum graph showing the response of Substrate Compound 2 incubated with 1 U/mL from β-lactamases from Enterobacter cloacae (with 10% dimethyl sulfoxide) after 210 minutes.

DETAILED DESCRIPTION OF THE INVENTION

Industrial Applicability

Figure 1:
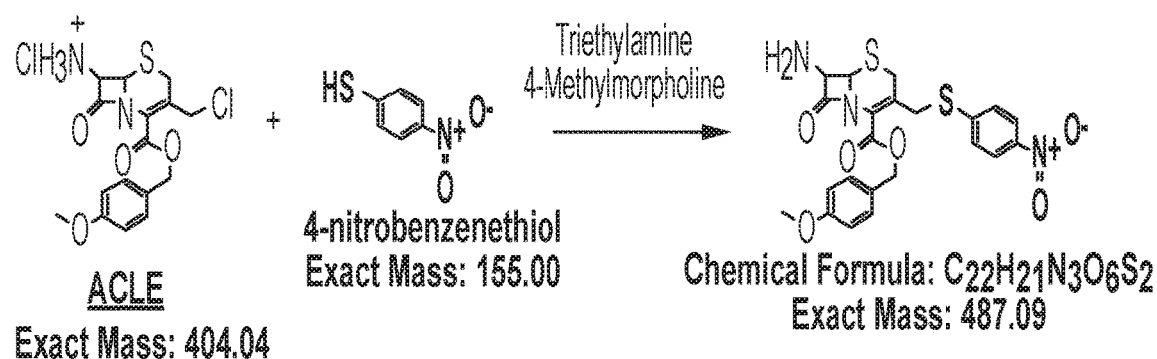
FIG. 1 is a synthetic scheme showing a chemical equation for the synthesis and chemical structure of Compound 1 (ANT) from 7-amino-3-chloromethyl-3-cephem-4-carboxylic acid β-methoxybenzyl ester hydrochloride (ACLE) and 4-nitrobenzenethiol (NBT).

Chromogenic β-lactam molecules of the invention can be attached to in multifunctional materials (e.g., wound dressing hydrogels), thus showing a localized color change in the presence of β-lactamase-producing bacteria.

Definitions

The meaning of some terms and phrases used in the specification, examples, and appended claims, are listed below. Unless otherwise defined, all technical and scientific terms used have the same meaning as commonly understood by one of ordinary skill in the chemical art. If there is an apparent discrepancy between the usage of a term in the chemical art and its definition provided, the definition provided within the specification shall prevail.

The terms "comprises" and "comprising" should be interpreted as referring to elements, components, or steps in a non-exclusive manner, indicating that the referenced elements, components, or steps may be present, used, or combined. The singular terms "a," "an," and "the" include plural referents unless context clearly indicates otherwise. Similarly, the word "or" should include "and" unless the context clearly indicates otherwise. The abbreviation "e.g."

is used to indicate a non-limiting example. Thus, the abbreviation "e.g." is synonymous with the term "for example."

Unless stated otherwise, or implicit from context, these terms and phrases include the meanings below.

"About" has the plain meaning of "approximately." When used with percentages, "about" means±1%. Otherwise, "about" means to be within a range of normal tolerance in the chemical art, e.g., within 2 standard deviations of the mean.

"LC" has the chemical art meaning of liquid chromatography. HPLC" is high-pressure liquid chromatography. In HPLC, those of skill in the chemical art inject a liquid sample into a stream of solvents. Together, the sample and solvents are forced, at high pressure, through an analytical column. Depending on the column and solvents, some chemicals exit the column at different times. At the end of the column are an ultraviolet (UV) light source and a photodetector. When an appropriate wavelength is selected, the analyte can be detected by a change in absorbance as it exits the column. The absorbance is plotted over time as a chromatogram. See, Karger, "HPLC: Early and recent perspectives," Journal of Chemical Education, 74(1), 45 (1997). Those of ordinary skill in the chemical laboratory art can supplement HPLC methods with other analytical techniques such as mass spectrometry. Zeng & Kassel, "Developments of a fully automated parallel HPLC/mass spectrometry system for the analytical characterization and preparative purification of combinatorial libraries," Analytical Chemistry, 70(20), 4380-4388 (1998); Shockcor et al., "Combined HPLC, NMR spectroscopy, and ion-trap mass spectrometry with application to the detection and characterization of xenobiotic and endogenous metabolites in human urine," Analytical Chemistry, 68(24), 4431-4435 (1996).

"ACLE" is the cephalosporin derivative 7-amino-3-chloromethyl-3-cephem-4-carboxylic acid p-methoxybenzyl ester hydrochloride. ACLE is commercially available from AK Scientific (Union City, CA, USA).

"CENTA" is a chromogenic β-lactamase molecule used as a diagnostic marker of β-lactamase production when the β-lactam ring is cleaved, and subsequent electron transfer leads to a structural change. Jones et al., J. Clinical Microbiol, 15(5): 954-958 (May 1982), first studied CENTA and set out the standards used to assess a new β-lactamase-susceptible chromogenic β-lactamase substrate. CENTA continues to be a medically and commercially important β-lactamase-susceptible chromogenic substrate. CENTA cannot practically detect β-lactamase-producing strains on agar plates, but CENTA has been useful for kinetic studies and the detection of the enzymes in crude extracts and chromatographic fractions. See, Bebrone et al., Antimicrobial Agents Chemother., 45, 1868-1871 (2001) and Jones et al., J. Am. Chem. Soc., 128, 6526-6527 (2006). CENTA is commercially available from MilliporeSigma (Billerica, MA, USA).

"Conjugated" refers to a chemical substance being reversibly combined with another chemical substance.

"Control" sample is a sample of known composition analyzed along with test samples to evaluate the accuracy of an analytical procedure. Control samples are essential for the quality control and assurance procedures those of skill in the chemical art use to eliminate the inaccuracy of laboratory results.

"Formulation" has the medical art definition of a material or mixture prepared according to a particular formula to produce a final medicinal product. In this specification, a formulation comprises a β-lactam molecule included in or conjugated to another molecule to have a medically useful purpose, such as a wound dressing, an ointment, a cream, a gel, a hydrogel, or a bandage.

"Hydrogel" has the chemical art definition of a gel in which the liquid component is water. Hydrogel products constitute a group of polymeric materials, the hydrophilic structure of which renders them capable of holding large amounts of water in their three-dimensional networks. See, Mohite & Adhav, "A hydrogels: Methods of preparation and applications," Intl. J. Adv. Pharm., 06(03), 79-85 (2017).

"Leaving group, in the chemical art, is a molecular fragment that departs with a pair of electrons in heterolytic bond cleavage.

"Macromolecule" is a molecule containing many atoms, such as a protein, nucleic acid, or synthetic polymer.

"Maleimide" is an unsaturated imide that is an important building block in organic synthesis. The term maleimide also describes a class of derivatives of the parent maleimide where the —NH group is replaced with alkyl or aryl groups such as a methyl or phenyl, respectively. As used in this specification, maleimide is 3-maleimidopropionic acid. Maleimide is commercially available from TCI Chemicals (Tokyo, Japan).

"Mass spectrometry" (MS) is an analytical technique that ionizes chemical species and sorts the ions based on their mass-to-charge ratio. A mass spectrum measures the masses within a sample. Mass spectrometry is useful for broad and high-throughput metabolic screening. Zampieri et al., Current Opinion in Chem. Bio. 36, 15-23 (2017). Advances in statistical tools and databases support mass spectrometry. See, Brown et al., Analyst, 134(7), 1322-32 (2009) and Wishart et al., Nucleic Acids Res. 4(46), 608{617 (2018). "Mass spectrometry" (MS) is an analytical technique that ionizes chemical species and sorts the ions based on their mass-to-charge ratio. A mass spectrum measures the masses within a sample. Mass spectrometry is useful for broad and high-throughput metabolic screening. Zampieri et al., Current Opinion in Chem. Bio. 36, 15-23 (2017). Advances in statistical tools and databases support mass spectrometry. Brown et al., Analyst, 134(7), 1322-32 (2009); Wishart et al., Nucleic Acids Res. 4(46), 608{617 (2018). Sub-zeptomole mass spectrometry and nanomolar concentration detection have been available for nearly two decades. Belov et al., Anal. Chem. 72(10), 2271-2279 (2000); Tang et al., J. Bact. 189, 940-949 (2007).

"NBT" is the chromophore 4-nitrobenzenethiol. NBT is commercially available from TCI Chemicals (Tokyo, Japan).

"Nitrocefin" is a chromogenic β-lactamase molecule used as a diagnostic marker of β-lactamase production when the β-lactam ring is cleaved, and subsequent electron transfer leads to a structural change. Nitrocefin is a chromogenic β-lactamase substrate. Nitrocefin hydrolysis can be directly monitored in the visible wavelength range, are of interest for the kinetic characterization of β-lactamases. The price of nitrocefin has increased recently because the chemical synthesis of nitrocefin is tedious. Nitrocefin is commercially available from P212121, LLC (Boston, MA, USA).

"NMR" is nuclear magnetic resonance, an analytical technique used in the chemical art that involved the absorption of electromagnetic radiation by an atomic nucleus having a magnetic moment when in an external magnetic field.

"PADAC" is a chromogenic β-lactamase molecule used as a diagnostic marker of β-lactamase production when the β-lactam ring is cleaved, and subsequent electron transfer leads to a structural change. PADAC is no longer commercially available. The chemical synthesis of PADAC is tedious.

"Primary amine" is an amine where an alkyl or aromatic group replaces one of three hydrogen atoms corresponding to ammonia. Primary alkyl amines include methylamine, most amino acids, and the buffering agent tris, while primary aromatic amines include aniline.

"Protected carboxylic acid group" is a carboxylic acid group on a molecule that is, during the preparing of organic compounds, chemically modified to prevent chemical reactivity of the functional carboxylic acid group, with the goal being to obtain chemoselectivity in a subsequent chemical reaction. The reversible protection of carboxylic acid groups can be by the creation of methyl esters, benzyl esters, tert-butyl esters, esters of 2,6-disubstituted phenols (e.g., 2,6-dimethylphenol, 2,6-diisopropylphenol, 2,6-di-tert-butylphenol), silyl esters, orthoesters, or oxazoline.

"Shift in the absorbance spectrum" is a change in the absorbance of a substance undergoing a chemical reaction to a longer wavelength (red shift) or a shorter wavelength (blue shift), as measured by ultraviolet-visible light spectroscopy.

"Shift in the maximum absorbance peak" is a shift in the absorbance spectrum where the shift being measured is the shift in the wavelength of maximum absorption.

"Wound dressing" is a pad or compress applied to a wound to promote healing and protect the wound from further harm. A dressing was traditionally made of cloth, but can nowadays be made from many medically useful substances, such as polymers or hydrogels. Nowadays, dressing is usually sterile when initially applied. A dressing is in direct contact with the wound, as distinguished from a bandage, which is most often used to hold a dressing in place "β-lactam ring" is a four-membered cyclic amide. The β-lactam ring is part of the core structure of several antibiotic families, the principal ones being the penicillins, cephalosporins, carbapenems, and monobactams, which are, therefore, also called β-lactam antibiotics.

"β-lactamase" is an enzyme (from the class EC 3.5.2.6) produced by bacteria that enzyme breaks the β-lactam ring open, deactivating the molecule's antibacterial properties. β-lactamase from *Bacillus cereus*, β-lactamase from *Pseudomonas aeruginosa*, and β-lactamase from *Enterobacter cloacae* are commercially available from MilliporeSigma (Billerica, MA, USA). See, Bebrone et al., Antimicrobial Agents Chemother., 45, 1868-1871 (2001); Mirsalehian et al., Iranian J. Microbiol., 6, 306-310 (2014); and Seeberg, Tolxdorff-Neutzling & Wiedemann, Antimicrobial Agents Chemother., 23, 918-925 (1983).

Enablement

Those of ordinary skill in the chemical art may rely upon these publications for guidance as to how to make and use the invention.

U.S. Pat. No. 4,535,156 (Blumbach et al.) entitled "Chromogenic cephalosporin compound."

U.S. Pat. No. 7,396,926 (Tsien et al.) entitled "Beta-lactamase substrates having phenolic ethers."

U.S. Pat. No. 7,427,680 (Tsien et al.) entitled "Substrates for beta-lactamase and uses thereof."

U.S. Pat. No. 8,071,761 (Tsien et al.) entitled "Substrates for beta-lactamase and uses thereof."

U.S. Pat. No. 8,097,434 (Yang-Woytowitz et al.) entitled "Methods for the detection of beta-lactamases."

U.S. Pat. No. 8,883,772 (Sutton et al.) entitled "Broad spectrum beta-lactamase inhibitors."

U.S. Pat. No. 9,783,797 (Kaleko et al.) entitled "Beta-lactamases with improved properties for therapy."

European patent EP0034759B1 (Hoechst AG) entitled "Chromogen cephalosporins and process for their preparation."

Shao et al., "Enzyme responsive luminescent ruthenium(II) cephalosporin probe for intracellular imaging and photoinactivation of antibiotics resistant bacteria," Chemical Communications 48(12):1739-41 (November 2011).

Khan et al., "Rapid optical determination of β-lactamase and antibiotic activity," BMC Microbiol., 14:84 (Apr. 4, 2014)

Van Berkel et al., "Assay platform for clinically relevant metallo-β-lactamases," J. Med. Chem., 56 (17): 6945-6953 (2013).

Xiao et. al., "Novel fluorescent cephalosporins," Eur. J. Med. Chem. (November 2012).

Xie et al., Angewandte Chemie Intl. Ed., 53, 9360-9364 (2014), describing fluorescence detectors.

Bonnet, Antimicrobial Agents Chemother., 48(1), 1-14 (January 2004).

Device

The invention provides hydrogels comprising a chromogenic β-lactamase substrate (e.g., Conjugated Compound 4) that can be applied to a wound as an ointment or incorporated into a bandage. Hydrogel dressings usefully to hydrate the wound. Hydrogel dressings can come in several forms, including (a) amorphous hydrogel: a free-flowing gel, distributed in tubes, foil packets and spray bottles; (b) impregnated hydrogel: typically saturated onto a gauze pad, nonwoven sponge ropes and/or strips; and (c) sheet hydrogel: a combination of gel held together by a thin fiber mesh. For further information, see Hoque et al., Mol. Pharm., 14(4):1218-1230 (Apr. 3, 2017).

Method of Manufacture

The invention provides a method for synthesizing a chromogenic β-lactamase substrate-polymer conjugate as a platform for developing biomaterials (e.g., nanoparticles or hydrogels) that incorporate a detection functionality. See, FIG. 8, Synthesis Scheme 1.

The inventors successfully conjugated chromogenic β-lactamase substrate to polymers, as confirmed via mass spectrometry. This conjugate remained responsive to β-lactamases as demonstrated by the change in color in the presence of penicillinase. This functionalization allows those of ordinary skill in the chemical art to conjugate a chromogenic β-lactamase substrate to a broad range of polymers for use as diagnostic materials. These biomaterials can be placed on wounds to visualize a color change in situ if an infection by β-lactamase-producing bacteria develops, promoting appropriate treatment. Conjugation to a polymer could allow the formation of different types of biomaterials, even combined with existing wound treatment systems, for developing multifunctional therapeutics with convenient application to the injury site. The conjugate can also sequester the indicator compound within the biomaterial, preventing its release before it is needed.

The β-lactamase substrate was used to develop PEG and gellan hydrogels that changed color in the presence of β-lactamase. These β-lactamase substrates conjugate to a polymer backbone for direct and easy point-of-care colorimetric detection of infections by β-lactamase-producing bacteria. These multifunctional biomaterials are useful for the prevention, detection, and treatment of bacterial infections.

Kits for a Method of Diagnosis

Many commercialized products leveraging chromogenic β-lactamase substrates are kits targeted towards small-benchtop assays or culture medium-formulations/ready-to-use agar plates. Those of skill in the chemical art can use the chromogenic β-lactamase substrates provided in this specification in kits targeted towards small-benchtop assays or culture medium-formulations/ready-to-use agar plates by substituting chromogenic β-lactamase substrates provided in this specification for the prior art chromogenic β-lactamase substrates., See, e.g., U.S. Pat. No. 8,097,434 (Yang-Woytowitz et al.).

The kit containing a detectable β-lactamase substrate (e.g., Substrate Compound 2) for detecting β-lactamase can comprise a lysis reagent, an agent that promotes the stabilization of the lysis reagent, and an additional agent, e.g., an agent that enhances the lysis of a bacterial cell by a lysis reagent (e.g., a metal chelator such as EDTA or EGTA). In a twenty-eighth embodiment, the lysis reagent lyses the bacterial cells but does not interfere with either the hydrolysis of the β-lactamase substrate. In a twenty-ninth embodiment, the lysis reagent is a detergent, such as mild non-denaturing detergent (e.g., Triton® X-100 or CHAPS). In a thirtieth embodiment, the lysis reagent is an enzyme or another agent that promotes the lysis of a bacterial cell. Non-limiting examples of such an enzyme include lysozyme, labiase, lysostaphin, achromopeptidase, and mutanolysin. In a thirty-first embodiment, the agent that promotes the stabilization of the lysis reagent is thermal stable. In a thirty-second embodiment, the kit contains components in a liquid composition; an agar plate; a paper strip; a paper disk; a tablet, in wells of a plate (e.g., a microtiter plate), tray, or cassette; in one or more tubes, (e.g., a test tube or Eppendorf tube), an array of tubes, a cassette or a panel, on or in a solid support, such as a paper strip, a paper disk. In a thirty-third embodiment, the compositions in the kits are dried and present in the wells of a well, tube, or panel. In a thirty-fourth embodiment, the kits further comprise one or more of an AmpC inhibitor; a serine β-lactamase inhibitor in an amount sufficient to inhibit an extended-spectrum β-lactamases (ESBL) and an "older-spectrum" β-lactamase ("OSBL," e.g., TEM-1, SHV-1, or OXA-1), but not a class A serine carbapenemase; a metal chelator; and another extended-spectrum β-lactamases (ESBL) inhibitor.

The following EXAMPLES are provided to illustrate the invention, and should not be considered to limit its scope.

Example 1

Synthesis of Compound 1 (Protected ANT)

The purpose of this EXAMPLE was to synthesize a chromogenic β-lactamase substrate. To synthesize the protected β-lactam Compound 1, the inventors conjugated ACLE and NBT at the ACLE 3'-position to synthesize Compound 1.

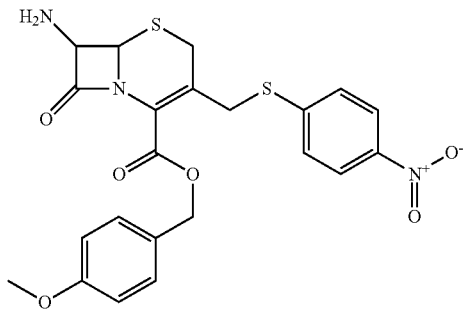 [SMILES: COc1ccc(COC(=O)C2=C(CSc3ccc([N+](=O)[O-])cc3)CSC3C(N)C(=O)N23)cc1]

See, synthesis scheme of FIG. 1. ACLE (600 mg, 0.148 mmol) was dissolved in twenty mL dichloromethane and stirred at room temperature (23° C.). TEA (390 µL, 0.281 mmol) was slowly added in three portions over twenty minutes to the ACLE mixture. NMM (200 µL, 0.18 mmol) and NBT (370 mg, 0.24 mmol) were added sequentially thereafter. The reaction was stirred at room temperature for one hour with samples taken every fifteen minutes for thin-layer chromatography (TLC) analysis (30% hexanes/ 70% ethyl acetate). After one hour, the dichloromethane was evaporated using a Buchï rotary evaporator.

The ACLE and NBT conjugate was purified using column chromatography (silica gel, 70% to 100% gradient ethyl acetate in hexanes as eluent) to yield the purified Compound 1 product (586 mg, 81% yield).

The inventors performed a mass spectrum of the conjugate, which showed that the conjugate does not undergo a color change, whether incubated in penicillinase or phosphate-buffered saline only.

All the peaks showed up in $^1$H-NMR. $^1$H-NMR for was recorded on a Bruker 400 MHz instrument, with six mg of Compound 1 dissolved in deuterated-dimethyl sulfoxide to confirm conjugation. Deuterated dimethyl sulfoxide (DMSO-d6) and deuterium oxide are commercially available from Cambridge Isotope Laboratories (Andover, MA, USA). The ratio of ANT to maleimide was 1:1, confirming the conjugation and the removal of any free maleimide.

The methoxybenzyl protecting group prevents modification of the cephalosporin's carboxylic group, which is a recognition site for enzyme-substrate interactions. See, Morandi et al., J. Am. Chem. Soc., 125, 685-695 (2003). Unlike CENTA's chromophore, which has a carboxylic group susceptible to possible modification, the chromophore here is unmodified during the reactions.

The primary amine at the 7'-position can subsequently conjugate to polymers.

Example 2

Deprotection of Compound 1 to Form Substrate Compound 2 (ANT)

Initial efforts in synthesizing Substrate Compound 2. The inventors first tried a method of dissolving in dimethyl sulfoxide, adding methanol, precipitating products, and removing supernatant. Methanol is commercially available from Thermo Fisher Scientific (Waltham, MA, USA). Dimethyl sulfoxide (DMSO) is commercially available from MilliporeSigma (Billerica, MA, USA). Because the product would not crash out after adding methanol, the inventors determined that this method was not optimal. Next, the inventors removed methanol and added a bit of water, after which the product immediately precipitated and was spun down out of solution and collected. However, the inventors could not remove the protecting group by-products.

Figure 11:
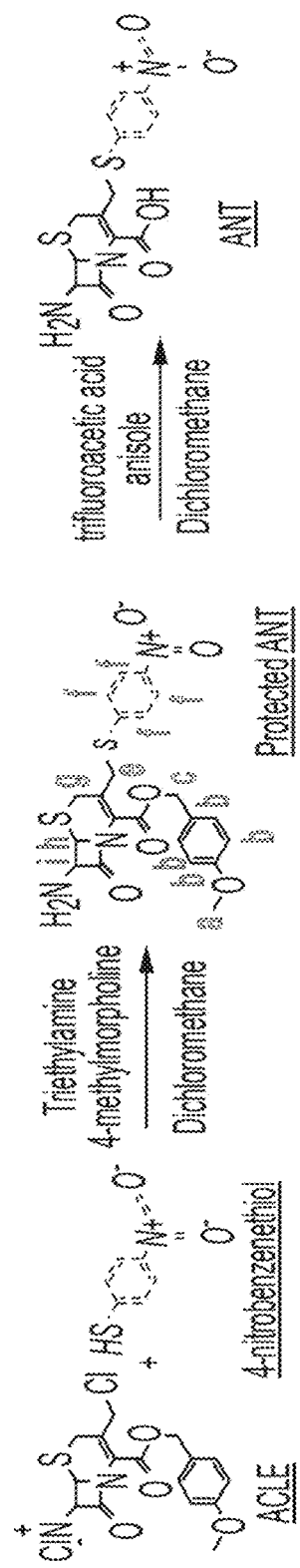
FIG. 11 is a synthetic scheme for β-lactamase substrate synthesis and deprotection.

Synthesis scheme. Compound 1 was deprotected to yield Substrate Compound 2 to characterize the colorimetric and enzyme kinetic response in the presence of β-lactamases. The deprotection conditions were (a) 70 mg Compound 1 in thirty-five ml dichloromethane, (b) seven ml anisole added, (c) seven ml trifluoroacetic acid added, and (d) incubation on ice for four hours. In a specific deprotection, Compound 1 was deprotected in TFA:anisole:DCM at a 1:1:5 volumetric ratio on ice for four hours. See, FIG. 11.

The dichloromethane and trifluoroacetic acid were evaporated under reduced pressure. The anisole was removed through nitrogen bubbling. Ultra-high-purity nitrogen gas (99.999%) is commercially available from Corp Brothers, Inc. (Providence, RI, USA).

The syntheses were performed in 10% dimethyl sulfoxide since Substrate Compound 2 is not soluble in aqueous conditions. Dimethyl sulfoxide (DMSO) is commercially available from MilliporeSigma (Billerica, MA, USA).

The deprotected conjugate was dissolved in DMSO at a concentration of approximately eight mg/ml and diluted with methanol. Methanol is commercially available from Thermo Fisher Scientific (Waltham, MA, USA). The suspension was left at 4° C. overnight to precipitate.

Afterward, the suspension was centrifuged for thirty minutes at 4° C. and rpm to obtain a pellet. The supernatant was removed and the pellet redissolved in dimethyl sulfoxide. The rinsing process was repeated and after the second rinse. The final product was frozen, lyophilized, and stored at −20° C. (45% yield).

Nuclear magnetic resonance analysis confirmed conjugation. $^1$H-NMR was recorded on a Bruker 400 MHz instrument with six mg of Substrate Compound 2 dissolved in deuterated-dimethyl sulfoxide. Deuterated-dimethyl sulfoxide (DMSO-d6) and deuterium oxide are commercially available from Cambridge Isotope Laboratories (Andover, MA, USA). $^{13}$C-NMR and $^2$D-NMR were run on a Bruker 600 MHz instrument with six mg of Substrate Compound 2 dissolved in deuterated-dimethyl sulfoxide.

Example 3

Synthesis of Compound 3 (ANT-Maleimide)

Figure 12:
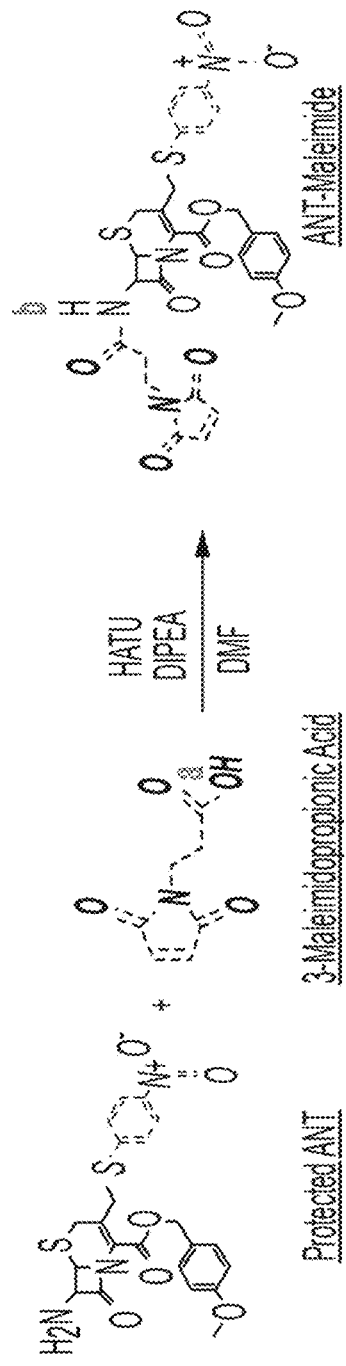
FIG. 12 is a synthetic scheme for β-lactamase substrate-maleimide synthesis.

Compound 1 (105.7 mg, 0.388 mmol) was combined with maleimide (238.69 mg, 1.55 mmol) and dissolved in three mL dimethylformamide. hexafluorophosphate azabenzotriazole tetramethyl uronium (HATU) (393.8 mg, 1.861 mmol) was added to the mixture. See, FIG. 12. The reaction was stirred for 15 minutes at room temperature before adding N,N-diisopropylethylamine (DI PEA) (256.6 μL, 2.713 mmol). The reaction could proceed at room temperature for seventy-five minutes and monitored through TLC (20% ethyl acetate/80% hexanes). TLC Silica Gel 60 on glass plates is commercially available from MilliporeSigma (Billerica, MA, USA).

The crude reaction was transferred to a separatory funnel and partitioned between dichloromethane and 0.1 M HCl to separate the layers. The dichloromethane was rinsed again with HCl and then rinsed twice with water. All experiments used ultrapure deionized water (18.2 MΩ·cm, commercially available from MilliporeSigma, Billerica, MA, USA).

The combined organic layers were washed with brine and dried over sodium sulfate. The dichloromethane was then evaporated at reduced pressure. The conjugate was stored at −20° C. Compound 3 was dissolved in dimethyl sulfoxide at a concentration of approximately fifty mg/ml and diluted with water. The suspension was stored at 4° C. overnight. Afterward, the suspension was centrifuged for twenty minutes at 4° C. and 5000 rpm. The supernatant was removed at the rinsing process was repeated. After the final rinse, the product was frozen, lyophilized, and stored at −20° C. (60% yield).

Six mg of Compound 3 dissolved in deuterated-dimethyl sulfoxide were tested using $^1$H-NMR on a Bruker 400 MHz instrument to confirm conjugation. Deuterated dimethyl sulfoxide (DMSO-d6) and deuterium oxide are commercially available from Cambridge Isotope Laboratories (Andover, MA, USA).

$^1$H-NMR indicated the disappearance of the 3-maleimidopropionic acid carboxylic group proton at 12.36 ppm, along with the appearance of the newly formed amide's proton split at 8.98 and 9.06 ppm.

Example 4

β-Lactamase Substrate-Polymer Conjugates—PEG Hydrogel Formation

The inventors conjugated a β-lactamase substrate to a commonly used polymer to form diagnostic hydrogels. Poly(ethylene glycol) (PEG) was chosen as a model polymer because it is used extensively in biomaterials such as hydrogels, nanoparticles, and coatings for various biomedical applications given its biocompatibility and tunability. See, Zhu, J. Biomaterials, 31, 4639-4656 (2010) and Hamley, Conjugates Biomacromolecules, 155, 1543-1559 (2014).

For easy conjugation of the β-lactamase substrate to polymers, the inventors first functionalized Compound 1 with a maleimide group. This synthetic step allows for polymer conjugation via modular click-chemistry under mild conditions such as maleimide-thiol Michael-type addition or a furan-maleimide Diels-Alder reaction. 3-maleimidopropionic acid was conjugated to Compound 1 through amidation via its 7'-position primary amine, yielding Compound 3. See, FIG. 12

Next, the inventors conjugated Compound 3 to a linear, short PEG chain to investigate the effects of PEG addition on color change and enzyme kinetics. The inventors conjugated Compound 3 to methoxy-PEG-thiol (mPEG-SH) (1.7 kDa) via Michael-type addition click reaction forming Conjugated Compound 4.

Figure 13:
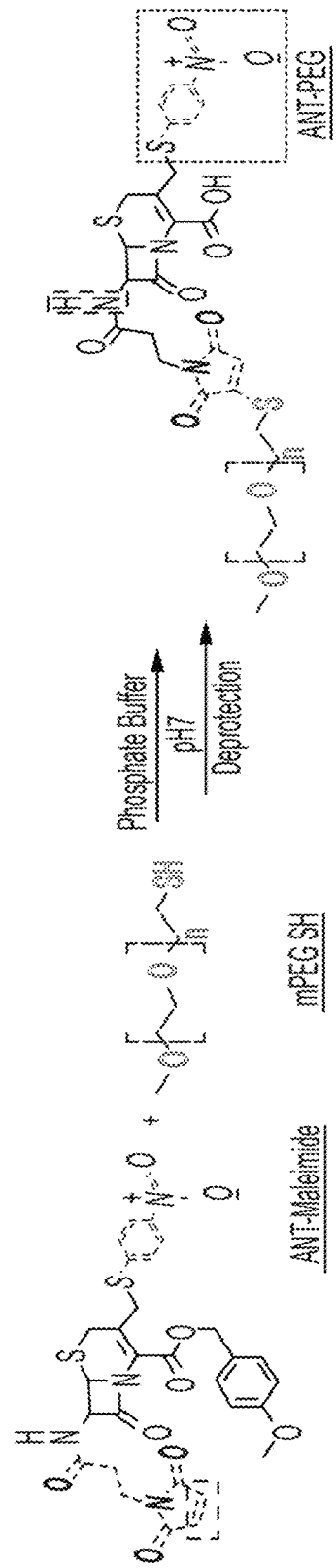
FIG. 13 is a synthetic scheme for the synthesis of Conjugate 4.

Compound 3 was conjugated to mPEG-thiol by a Michael-type addition in 0.15 M sodium phosphate buffer (pH 7) at room temperature for sixteen hours. Methoxy-poly (ethylene glycol)-thiol (mPEG-thiol) (average MW 1.7 kDa) is commercially available from Laysan Bio, Inc (Arab, AL, USA). See, FIG. 13.

Conjugated Compound 4 was then dialyzed in water for six hours, frozen, and lyophilized. Ultrapure deionized water (18.2 MΩ·cm, commercially available from MilliporeSigma, Billerica, MA, USA) was used in all experiments. Spectra/PorQ® dialysis membrane pre-treated 1 kDa and 50 kDa molecular weight cut off (MWCO) regenerated cellulose dialysis tubing is commercially available from Spectrum Labs Inc (Rancho Dominguez, CA, USA). Dialysis tubing (1 kDa and 50 kDa) is also commercially available from Thermo Fisher Scientific (Waltham, MA, USA).

Conjugated Compound 4 was deprotected in TFA:anisole: DCM at a 1:1:5 volumetric ratio on ice for three hours. The dichloromethane and trifluoroacetic acid were evaporated under reduced pressure. The conjugate was precipitated and rinsed in cold diethyl ether (centrifuged at 4,000×g for five minutes, −10° C.; 2×). Last, the conjugate was dialyzed in water for twenty-four hours, frozen, and lyophilized. Conjugation was confirmed using 1H-NMR, matrix-assisted laser desorption time of flight (MALDI-TOF) mass spectrometry, and size exclusion chromatography, using a Sepax Zenix SEC-150, 25° C., Mobile phase: 0.1 M PB, 0.350 mL/min. See, FIG. 13.

The conjugation was confirmed by $^1$H-NMR, where the disappearance of the maleimide protons at 7.0 ppm and the formation of a new signal at 4.0 indicate the formation of the thiol-maleimide adduct. The other protons on the adduct should have appeared in the region of 2.4-3.2 ppm. See, Northrop, Frayne & Choudhary, Polymer Chemistry 6, 3415-3430 (2015). In our case, this signal is obscured by the PEG repeating unit protons.

Figure 14:
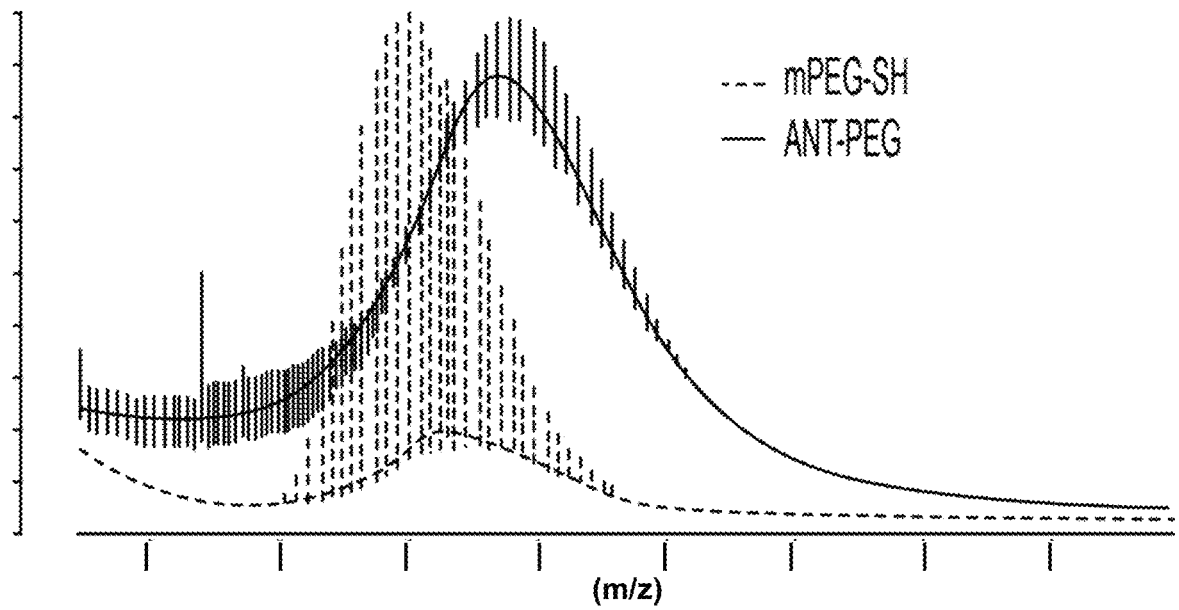
FIG. 14 shows size exclusion chromatograms of absorbance at 345 nm of 1 mg/mL, for mPEG-SH or Conjugated Compound 4 incubated with 200 U/mL β-lactamase or phosphate-buffered saline for three hours at 37° C. Methoxy-poly(ethylene glycol)-thiol (mPEG-thiol) (average MW 1.7 kDa) is commercially available from Laysan Bio, Inc (Arab, AL, USA).

Matrix-assisted laser desorption ionization-time of flight (MALDI-TOF) mass spectrometry showed a shift in the molecular weight distribution of the conjugate compared to unmodified mPEG-SH (suggesting an average MW increase of approximately 383 Da), indicating successful conjugation of 3 to PEG. See, FIG. 14.

Figure 15:
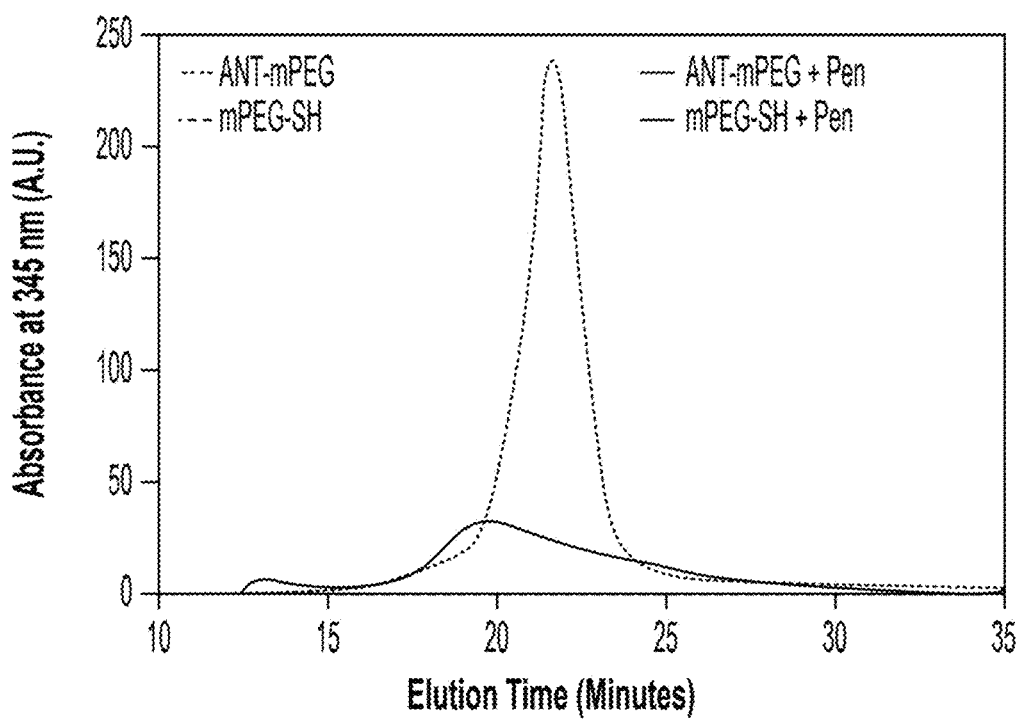
FIG. 15 is a MALDI-TOF spectrum chart of Conjugated Compound 4 and mPEG-SH.

Conjugated Compound 4 and unmodified mPEG-SH were also compared using size exclusion chromatography (SEC). The UV absorbance detector showed an appearance of a signal at 345 nm, the characteristic Amax, where Conjugated Compound 4 elutes (indicated by refractive index detector). mPEG-SH showed no absorbance signal, also indicating successful conjugation. See, FIG. 15.

Both size exclusion chromatography and NMR indicated that any free, unconjugated Compound 3 had been successfully removed. Aqueous solubility of the substrate was also improved, promoting its use in clinical situations.

In the presence of β-lactamase from *Bacillus cereus*, the solution of Conjugate 4 changed color from clear to a bright yellow. The spectral scan showed a decrease in the peak at 260 nm and the characteristic shift in Amax. See, FIG. 16. By size exclusion chromatography, a decrease in the absorbance signal at 345 nm was evident after the conjugate was incubated with β-lactamase, indicating successful cleavage of NBT from the PEG conjugate. See FIG. 15.

The β-lactam-PEG hydrogels were more swollen than the control hydrogels, which the inventors expected because of incomplete crosslinking with β-lactam-PEG hydrogels, resulting in larger pore sizes and enhanced swelling. Approximately one of the four arms of PEG-4SH is occupied by Compound 3. The hydrogels were cut in half before solutions of phosphate-buffered saline or β-lactamase from *Bacillus cereus* were added.

Example 5

β-Lactamase Substrate-Polymer Conjugates—PEG Hydrogel Formation

Besides the synthesis in EXAMPLE 4, the inventors modified 20% w/v PEG hydrogels with Compound 3. Compound 3 (in DMSO) was incubated with 4-arm-poly(ethylene glycol)-thiol (PEG-4SH; 20 kDa) (in 0.1× phosphate-buffered saline pH 5) at a 4:1 thiol to maleimide molar ratio with shaking at 100 rpm at 37° C. for fifteen minutes. Maleimide-PEG-maleimide (mal-PEG-mal; 2 kDa) (in DMSO) was then added to the solution at a 1:1 thiol to maleimide molar ratio to form hydrogels. The solution (50 μL) was briefly vortexed then quickly transferred to a PDMS mold, incubated at 37° C. for forty-five minutes. The control non-responsive hydrogels were formed similarly without adding Compound 3.

The hydrogels were rinsed in methanol then dichloromethane (with shaking at room temperature). Trifluoroacetic acid and anisole were added to deprotect the carboxylic acid (on ice for four hours). After the deprotection, the hydrogels were thoroughly rinsed in dichloromethane, then methanol. Before the hydrogels were incubated with β-lactamases, they were rinsed and equilibrated in 1× phosphate-buffered saline overnight at 4° C.

Example 6

β-Lactamase Substrate-Gellan Conjugates

To demonstrate the substrate's conjugation ability to a range of polymers with varying molecular weight and biomaterial formation/gelation mechanisms, we conjugated the β-lactamase substrate to a naturally-occurring bulky polymer, gellan gum. Gellan gum has been used to develop physically and covalently modified hydrogels. See, Du et al., Macromolecular Bioscience, 12, 952-961 (2012); Shukla & Shukla, J. Materials Chemistry B, 6, 6444-6458 (2018); Annaka, Ogata & Nakahira, J. Physical Chemistry B, 104, 6755-6760 (2000); Osma-lek, Froelich & Tasarek, S. Intl. J. Pharma., 466, 328-340 (2014).

The inventors first modified gellan gum with furan, using the method of Silva et al., Biomaterials, 33, 6345-6354 (2012). The inventors next characterized the modified gellan gum using $^1$H-NMR, which confirmed furan functionalization (about 70% efficiency). The inventors then conjugated Compound 3 to the gellan backbone via Diels-Alder click chemistry, as described by Gandini, Progress in Polymer Science, 38, 1-29 (2013); Gauthier & Klok, Chemical Communications, 2591 (2008). See, FIG. 17.

$^1$H-NMR confirmed successful conjugation and subsequent deprotection of Compound 3. β-lactamase substrate-gellan hydrogels were formed with 1:1 (% weight ratio) substrate-gellan to unmodified gellan. These hydrogels were rinsed in 1× phosphate-buffered saline to remove any unbound Compound 3 and exposed to 1× phosphate-buffered saline or β-lactamase from *Bacillus cereus*.

Gellan was first purified using ion exchange resins as described by Kirchmajer et al., Carbohydrate Research, 388, 125-129 (2014). GelzanTMCM GelriteQ® gellan gum (deacetylated gellan with an average molecular weight of 1 M Da) is commercially available from MilliporeSigma (Billerica, MA, USA)

Gellan was then modified with furan as described by Silva et al., Biomaterials, 33, 6345-6354 (2012). Briefly, gellan was first dissolved in MES buffer (100 mM, pH 5.5) at 37° C. 2-(N-morpholino)ethanesulfonic acid (MES) buffer is commercially available from MilliporeSigma (Billerica, MA, USA).

DMTMM and furfurylamine were then added in a 4:1 M ratio of each reagent relative to the COOH group in gellan and stirred at 37° C. for 48 hours. DMTMM and furfurylamine are commercially available from MilliporeSigma (Billerica, MA, USA).

The solution was then dialyzed ($M_w$ cutoff=10 kDa) alternately against distilled water and 1× phosphate-buffered saline for three days. Water was then removed by lyophilization to obtain furan-modified gellan gum (furan-gellan) as a white product. 1H-NMR spectra were used to analyze the degree of furan substitution in deuterated water on a Bruker 400 MHz NMR spectrometer.

Furan-gellan was first dissolved in deionized water (4 mg/mL) at 37° C. Compound 3 (dissolved in DMSO at 15 mg/mL) was then added to gellan-furan in a 3:1 maleimide to furan ratio and stirred vigorously for 48 hours at room temperature. The conjugate β-lactamase substrate-gellan, Conjugated Compound 5) was dialyzed in DMSO:water (1:1) for twenty-four hours and then dialyzed in water for two days. The conjugate was then frozen and lyophilized. The substrate-gellan was deprotected in TFA:anisole:DCM at a volumetric ratio of 1:1:5 on ice for 4 hours. The dichloromethane and trifluoroacetic acid were evaporated under reduced pressure. The substrate-gellan was then precipitated and rinsed in cold diethyl ether overnight (centrifuged at 4,000×g for five minutes, −10° C.; 3×). The conjugate was then dissolved in dichloromethane. Next, dichloromethane was evaporated under reduced pressure to remove any remaining diethyl ether. The conjugate was then dissolved in water, frozen, and lyophilized. 1H-NMR was recorded on a Bruker 400 MHz instrument with six mg of substrate-gellan dissolved in deuterated-DMSO to confirm conjugation and removal of side products.

β-lactamase substrate-gellan hydrogels (see, Conjugated Compound 5 and FIG. 17) were formed in a 1:1 substrate-gellan:unmodified gellan wt % ratio. First, 1% w/v β-lactamase substrate-gellan was dissolved in 50% DMSO and 1% w/v unmodified gellan was dissolved in deionized water and stirred at 37° C. The solutions were then combined. One mM of $CaCl_2$) was added to the hydrogel solution. One hundred µL of gel solution was pipetted into square molds (5×5×3 mm) and gelled for one hour. Hydrogels were then removed and rinsed in 1× phosphate-buffered saline to remove any unbound ANT and remaining DMSO. The hydrogels were then stored at 4° C. for subsequent use in future experiments. One hundred µL of 400 U/mL penicillinase or 1× phosphate-buffered saline was added to hydrogels with and without the β-lactamase substrate-gellan conjugate. Images were taken at various time points to show a color change in β-lactamase substrate-gellan hydrogels exposed to penicillinase.

Example 7

Substrate Compound 2 Incubation with β-Lactamases from Several Bacteria

Evaluating enzymatic response against different classes of β-lactamases provides a better insight towards the colorimetric efficacy Substrate Compound 2.

Substrate Compound 2 was tested with a class B β-lactamase from *Bacillus cereus* (Bebrone et al., Antimicrobial Agents Chemother., 45, 1868-1871 (2001)). Substrate Compound 2 was tested with class C β-lactamases (from *Pseudomonas aeruginosa* (Mirsalehian et al., Iranian J. Microbiol., 6, 306-310 (2014)) and β-lactamase from *Enterobacter cloacae* (Seeberg, Tolxdorff-Neutzling & Wiedemann, Antimicrobial Agents Chemother., 23, 918-925 (1983)). These bacteria are present in many infections, including wounds. See, Bodey et al., Clinical Infectious Diseases, 5, 279-313 (2011) and Davin-Regli & Pages, Frontiers in Microbiology, 6, 392 (2015).

Figure 2:
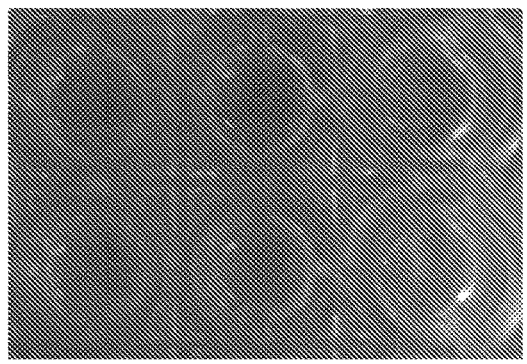
FIG. 2 is a photograph showing that Compound 1 (ANT) the presence of penicillinase after 1.5 hours at 37° C., showed a significant color change as compared to Compound 1 (ANT) in phosphate-buffered saline (PBS) under identical conditions.
Figure 3A:
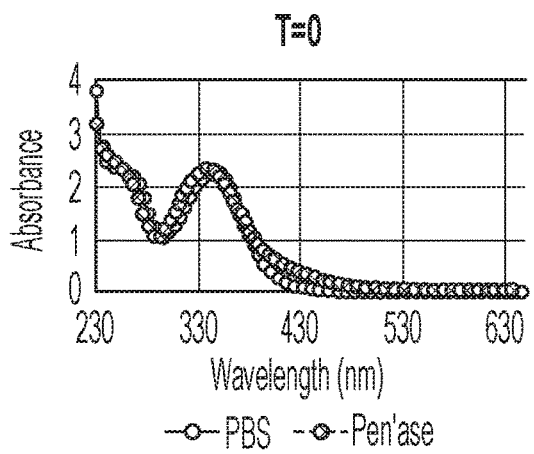
FIG. 3(A) shows a Compound 1 absorbance spectrum in phosphate-buffered saline or penicillinase immediately after adding the enzyme.
Figure 3B:
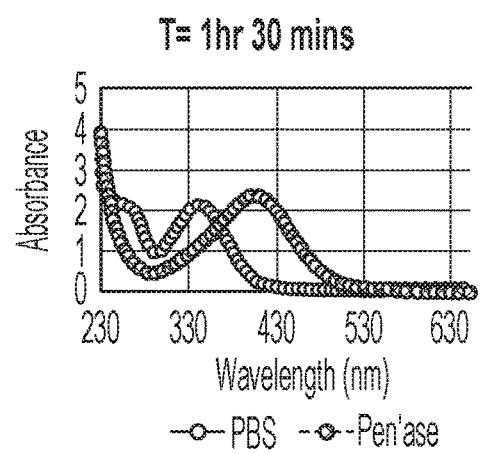
FIG. 3(B) shows an absorbance spectrum of Compound 1 (ANT) in phosphate-buffered saline or penicillinase after 1.5 hours at 37° C. As the β-lactam ring is cleaved by the enzymes, the peak at 260 nm disappears. As the leaving group is expulsed, the maximum absorbance peak shifts from 345 nm to 410 nm.
Figure 4:
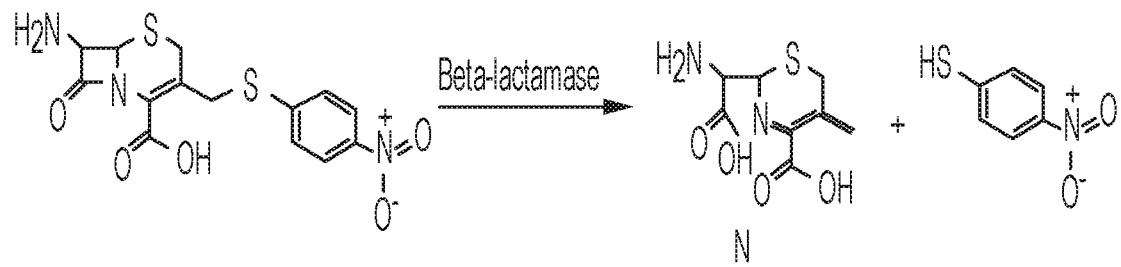
FIG. 4 is a degradation scheme showing the cleavage of the β-lactam ring by β-lactamase and the expulsion of the leaving group.
Figure 5:
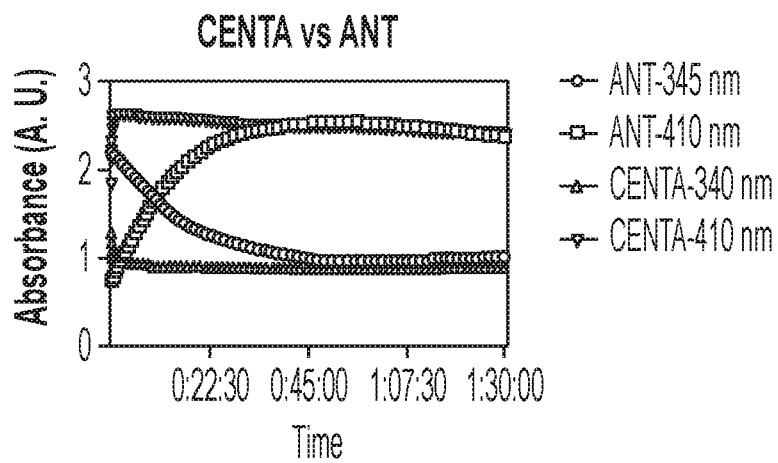
FIG. 5 is a comparison between Compound 1 (ANT) response and CENTA response. The absorbance/time chart shows that Compound 1 (ANT) and CENTA behave similarly in the presence of penicillinase, but CENTA reaches its maximum absorbance at a faster rate than Compound 1 (ANT).
Figure 6:
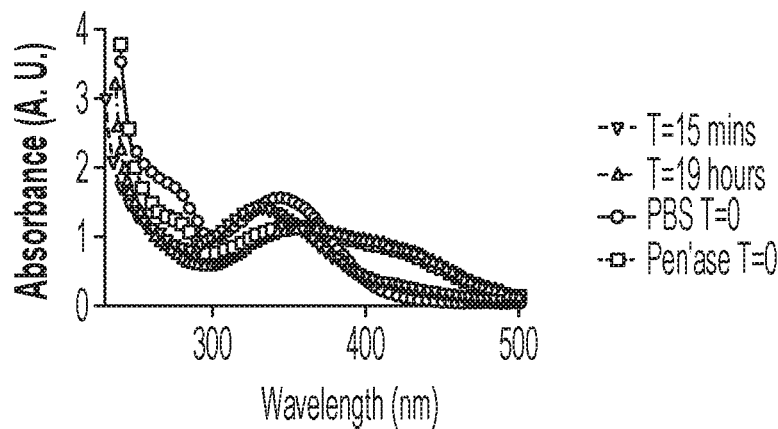
FIG. 6 is a chart showing deprotected ANT-maleimide in penicillinase, measuring the absorbance of conjugate at different time points. The peak at 260 nm, where the β-lactam ring absorbs, disappears after incubation with penicillinase confirming that the ring was cleaved and the molecule remains responsive
Figure 7:
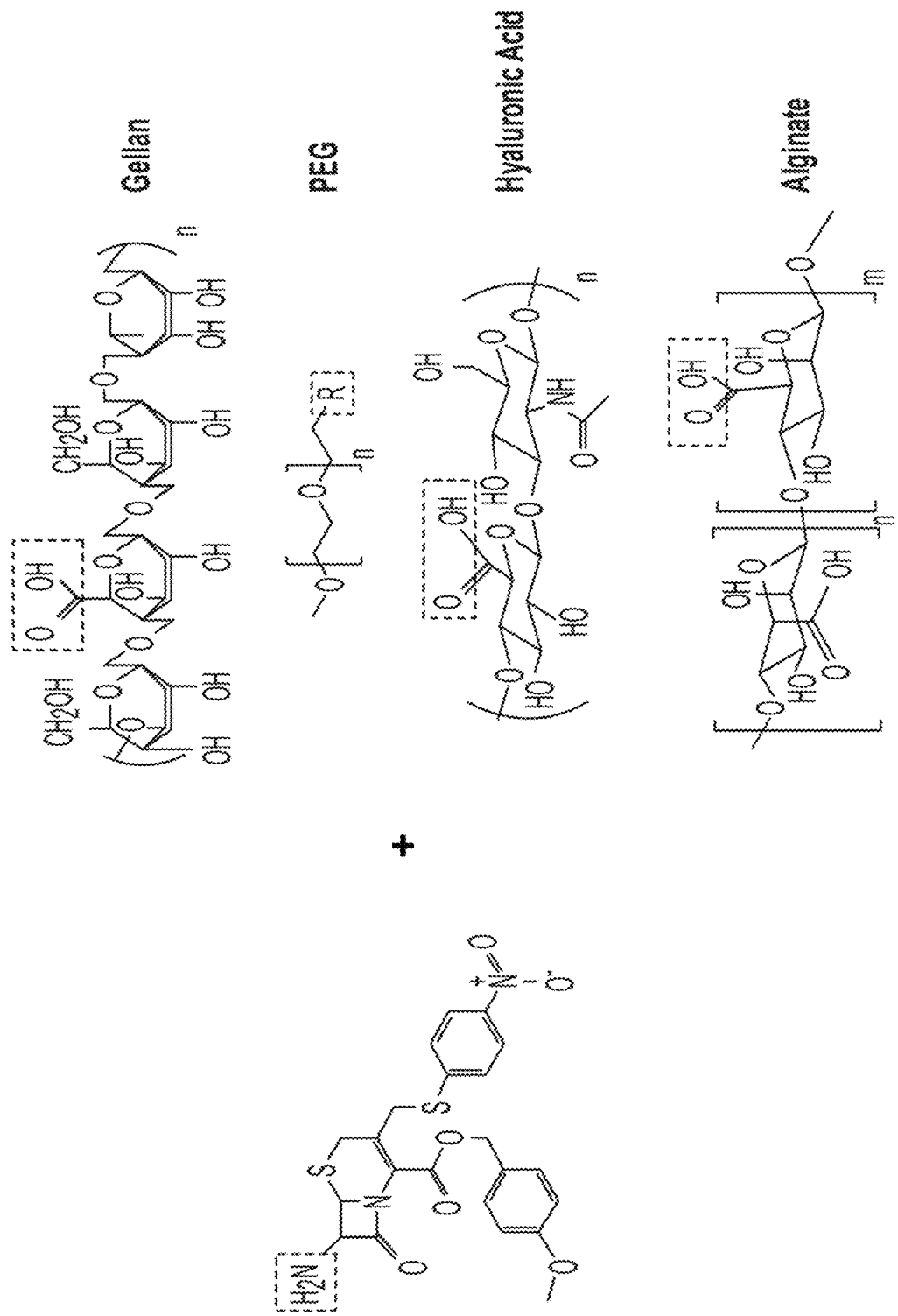
FIG. 7 is a schematic showing that those of ordinary skill in the chemical art can conjugate ANT to a range of polymers through its primary amine.
Figure 10:
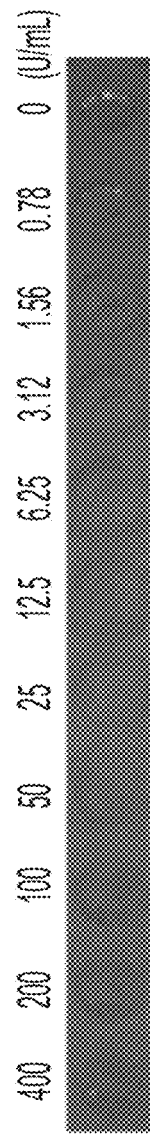
FIG. 10 shows photographic images of solutions of Substrate Compound 2 with different concentrations of β-lactamase from Bacillus cereus (U/mL) (with 10% dimethyl sulfoxide in 1× phosphate-buffered saline) after forty-five minutes in a 96-well plate.

Substrate Compound 2 successfully changed color from clear to yellow when mixed with any of the three β-lactamase enzymes. See, FIG. 2 and FIG. 10.

Figure 8A:
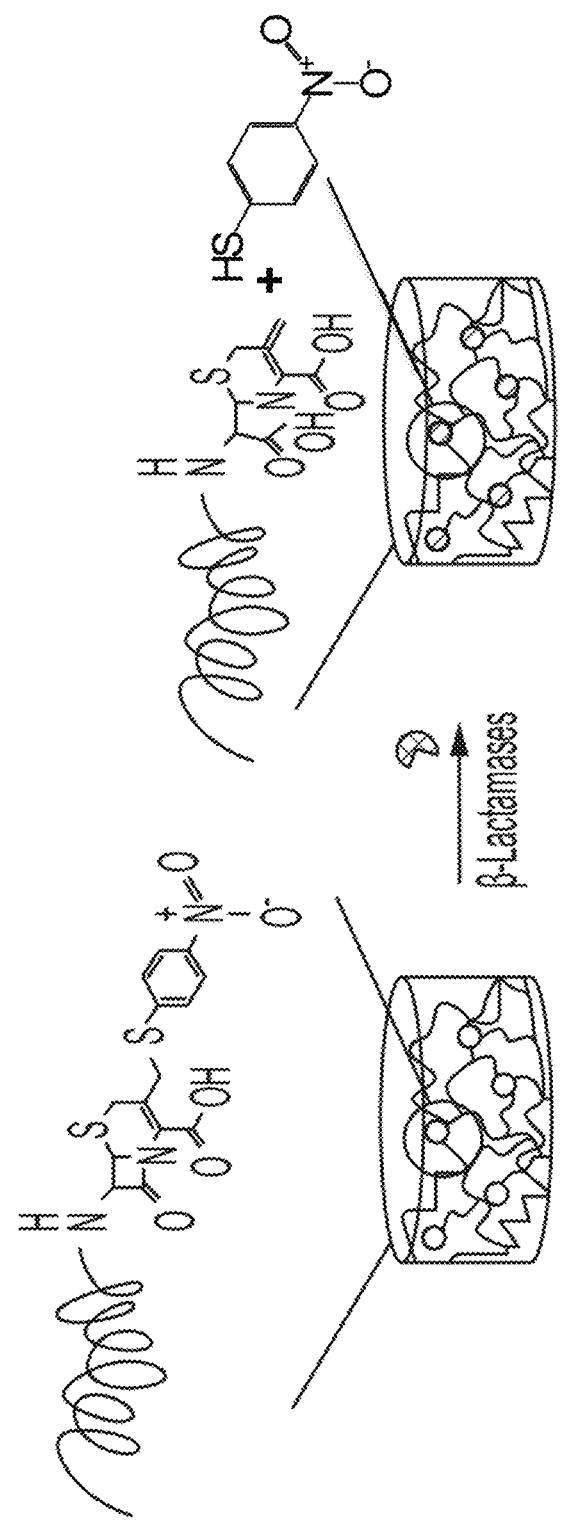
FIG. 8 shows synthesis scheme 1 for chromogenic β-lactamase-substrate and its polymer conjugates. ACLE=7-amino-3-chloromethyl-3-cephem-4-carboxylic acid p-methoxybenzyl ester, NBT=4-nitrobenzenethiol; TEA=triethylene amine; NMM=4-methylmorpholine; DCM=dichloromethane; HATU=1-[bis(dimethylamino)methylene]-¹H-1,2,3-triazolo[4,5-b]pyridinium 3-oxid hexafluorophosphate, or hexafluorophosphate azabenzotriazole tetramethyl uronium; DIPEA=N,N-diisopropylethylamine; DMF=dimethylformamide; and TFA=trifluoroacetic acid. TEA), DCM, TFA, NMM, HATU, and DIPEA are commercially available from MilliporeSigma (Billerica, MA, USA). ACLE is commercially available from AK Scientific (Union City, CA, USA).
Figure 8B:
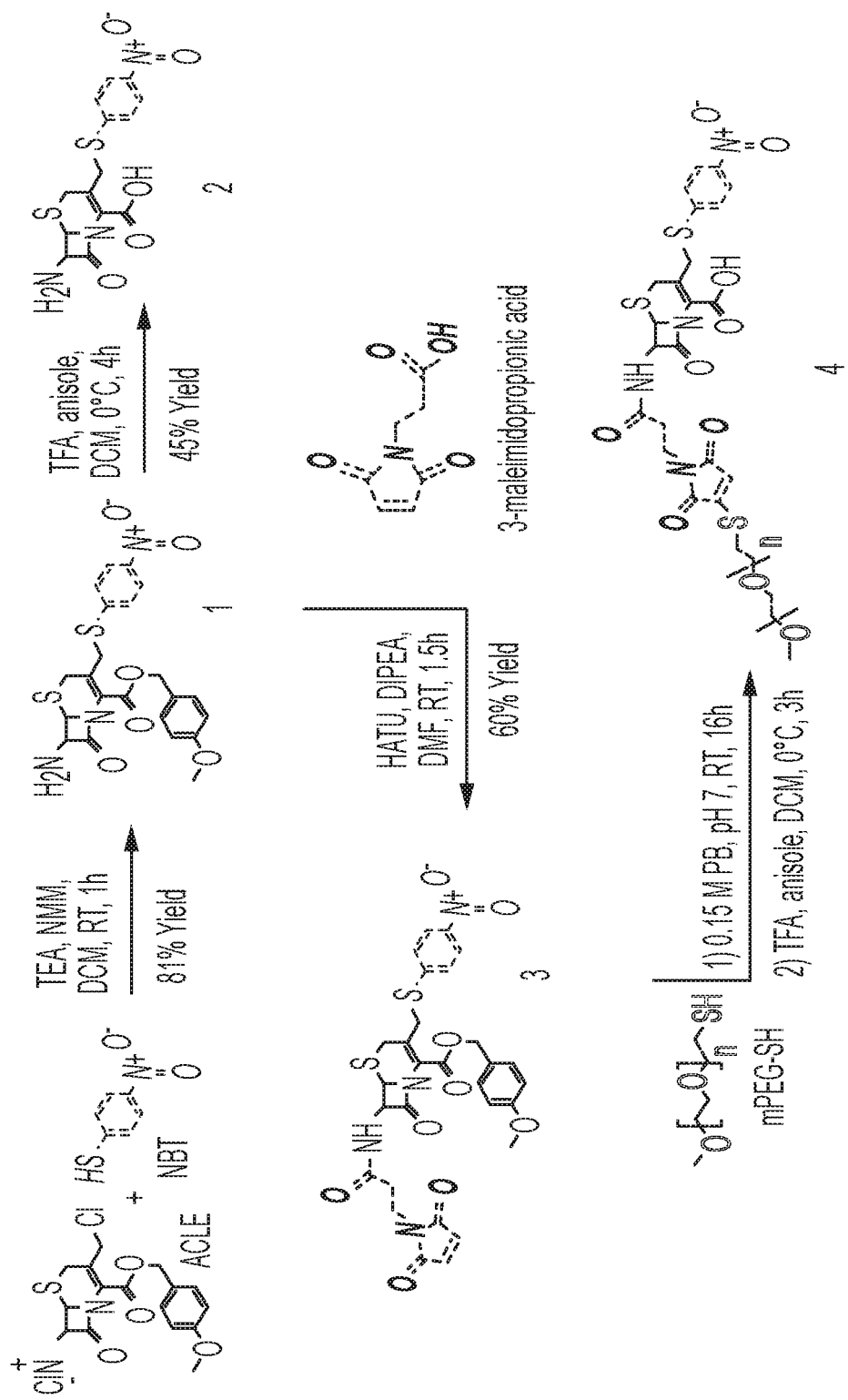
Figure 9:
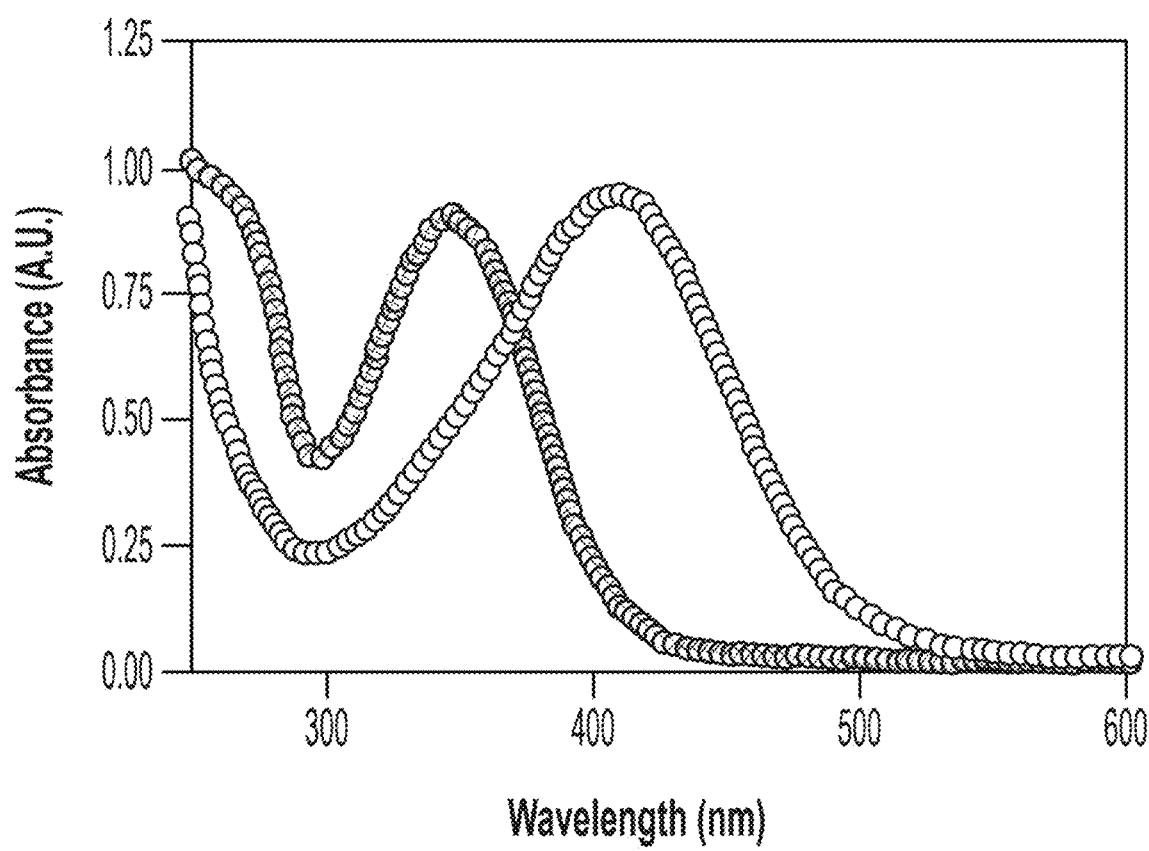
FIG. 9 shows the absorbance spectrum of Substrate Compound 2 incubated with 200 U/mL β-lactamase from Bacillus cereus (with 10% DMSO in phosphate buffer) after 90 minutes. One unit of β-lactamase hydrolyzes 1.0 µmole of benzylpenicillin per minute at pH 7.0 at 25° C.

The inventors also observed β-lactamase responses during measurements in the ultraviolet-visible (UV-vis) spectra. When β-lactamases cleave the β-lactam ring, the characteristic absorbance at 260 nm decreases and the chromogenic leaving group is expelled, as shown in FIG. 8, Synthesis Scheme 1. The expulsion of this chromogenic leaving group causes a red shift in the wavelength of maximum absorbance (Amax) from 345 to 410 nm.

The inventors measured the concentration-dependent absorbance shift in a spectral scan of Substrate Compound 2 with different concentrations (U/mL) of β-lactamase from *Bacillus cereus* or in phosphate-buffered saline after 45 minutes at 37° C. The absorbance signal at 410 nm increased to a maximum as a function of β-lactamase concentration. The inventors also performed these measurements for β-lactamase from *Pseudomonas aeruginosa* and *Enterobacter cloacae*.

The change in color of the β-lactamase substrate and the shifts in the spectral scan are β-lactamase concentration-dependent. The absorbance at 410 nm was plotted for each β-lactamase concentration, indicating a lower detection limit of approximately 3.12 units/mL (U/mL) for β-lactamases from *Bacillus cereus*.

96-well plate. Substrate Compound 2 was dissolved in DMSO at a concentration of two mg/ml. Fifteen µL of Substrate Compound 2 was added to a well of a 96-well plate. 135 µL of the respective β-lactamases was added to the same well. The samples of Substrate Compound 2 in β-lactamases from *Bacillus cereus* (200 U/mL in M sodium phosphate buffer, pH 7) were incubated for thirty minutes at 37° C. before the absorbance of the solution from 230 to 650 nm was measured using a BioTekQ®

Cytation3 plate reader. For the samples in *Pseudomonas aeruginosa* (50 U/mL in 0.15 M sodium phosphate buffer, pH 7), the absorbance was measured after ninety minutes at 37° C. (see FIG. 18). For the samples in *Enterobacter cloacae* (1 U/ml in M sodium phosphate buffer, pH 7), the absorbance was measured after three hours at 37° C. (see FIG. 19).

Further quantification of the β-lactamase response of Substrate Compound 2 to these enzymes was recorded by monitoring the change in absorbance at 260 nm, 345 nm, and 410 nm over the thirty minutes, ninety minutes, and three hours for the respective enzymes. Substrate Compound 2 detection limit testing was performed with β-lactamases from *Bacillus cereus*. 135 µL of β-lactamase at ten different concentrations (0.78-400 U/mL) was added to eleven wells of a 96-well plate along with one well with 135 µL of 0.15 M sodium phosphate buffer pH 7. Fifteen µL of Substrate Compound 2 dissolved in DMSO. Two mg/mL was added to each well, and the plate was incubated at 37° C. After forty-five minutes of incubation, the absorbance at 410 nm and the absorbance spectra from 230 nm to 650 nm were recorded.

Example 8

Michaelis-Menten Kinetics

To further characterize substrate-enzyme relationships between Substrate Compound 2 and β-lactamases, kinetic parameters were measured using Michaelis-Menten kinetics.

The inventors constructed Michaelis-Menten kinetics charts for Substrate Compound 2 and Conjugated Compound 4, as compared with CENTA and nitrocefin, for binding to β-lactamase from *Bacillus cereus*. The inventors also constructed Michaelis-Menten kinetics charts for Substrate Compound 2 and Conjugated Compound 4, as compared with CENTA and nitrocefin, for binding to β-lactamase from *Pseudomonas aeruginosa*. The inventors further constructed Michaelis-Menten kinetics charts for Substrate Compound 2 and Conjugated Compound 4, as compared with CENTA and nitrocefin, for binding to β-lactamase from *Enterobacter cloacae*.

The enzymatic activity of Substrate Compound 2 and Conjugated Compound 4 was measured against β-lactamases from *Bacillus cereus*, *Pseudomonas aeruginosa*, and *Enterobacter cloacae*. Parameters were determined for Substrate Compound 2 and commercially available chromogenic β-lactamase substrates CENTA and nitrocefin as comparisons, using different β-lactamases. All kinetic experiments were performed for concentrations of Substrate Compound 2 ranging from 0.025-0.2 mg/mL with 10% DMSO, and concentrations of 4 ranging from 1.5-12.1 mg/mL in 0.15 M sodium phosphate buffer pH 7 at 37° C. Hydrolysis of Substrate Compound 2 was measured by continuously recording the change in absorbance at 410 nm on a BioTekQ® Cytation3 plate reader. The $k_M$, $k_{cat}$, and $V_{Max}$ values were calculated through the initial velocities and the direct fitting of the Michaelis-Menten curve to the

Example 9

Substrate Compound 2 Antibacterial Effect

The inventors confirmed that the β-lactamase substrate did not have antibacterial effects on β-lactamase-producing bacteria, which could limit its usefulness as a tool to detect these bacteria against several bacteria species tested (Methicillin-resistant Staphylococcus aureus (MRSA), Escherichia coli, Pseudomonas aeruginosa, Enterobacter cloacae, and Bacillus cereus). Bacterial strains of Staphylococcus aureus (S. aureus 25923 and 29213), Escherichia coli 25922 (E. coli), Pseudomonas aeruginosa 27853, methicillin-resistant Staphylococcus aureus (BAA-1707) (MRSA) are commercially available from ATCC (Manassas, VA, USA).

Table 1 shows the comparative in vitro antibacterial efficacy of Substrate Compound 2 in different strains of bacteria.

| Bacteria | MIC (μg/mL) | Gram (+/−) | βL Producing |
|---|---|---|---|
| S. aureus 25923 | 8 | + | No |
| S. aureus 29213 | 8 | + | Yes |
| MRSA MW2 | >128 | + | Yes |
| B. cereus | >128 | + | Yes |
| E. coli 25922 | >128 | − | Yes |
| P. aeruginosa PA01 | >128 | − | Yes |
| E. cloacae | >128 | − | Yes |

Substrate Compound 2 was only antibacterial at the concentrations tested against the non-β-lactamase producing Staphylococcus aureus 25923 and against Staphylococcus aureus 29213, which produces low amounts of β-lactamases at a minimum inhibitory concentration of 8 μg/mL See, Lee et al., Microbial Drug Resistance 2014, 20, 568-574. These results are similar to those observed for chromogenic β-lactamase substrates PADAC, CENTA, and nitrocefin, which were not antibacterial against gram-negative species but had some activity against Staphylococcus aureus. See, Jones, Wilson & Novick, J. Clinical Microbiol., 15, 954-958 (May 1982) and Jones et al., J. Clinical Microbiol., 15, 954-958 (May 1982).

The antibacterial effect of Substrate Compound 2 was tested against Staphylococcus aureus, Escherichia coli, MRSA, and Pseudomonas aeruginosa in a microdilution assay. Substrate Compound 2 was dissolved in dimethyl sulfoxide at a concentration of 2.56 mg/mL and diluted to a concentration of 256 μg/mL in sterile phosphate-buffered saline. Substrate Compound 2 solutions and a control of 10% dimethyl sulfoxide in cation-adjusted Mueller Hinton broth (CMHB) or tryptic soy broth (TSB) were serially diluted 1:2 with cation-adjusted Mueller Hinton broth or tryptic soy broth in a 96-well plate. Cation-adjusted Muller-Hinton broth (CMHB) is commercially available from MilliporeSigma (Billerica, MA, USA).

Bacteria in its log phase was added to the wells at a final concentration of 105 CFU/mL. Positive controls of bacteria cultured in only media and negative controls of cation-adjusted Mueller Hinton broth or tryptic soy broth without bacteria were included. After eighteen hours of shaking at 100 rpm at 37° C., the optical density at 600 nm ($OD_{600}$) was measured using a BioTekQ® normalized bacteria density was calculated using equation 1:

$$\text{normalized bacteria density} = \frac{\text{sample } OD_{600} - \text{negative control } OD_{600}}{\text{positive control } OD_{600} - \text{negative control } OD_{600}}. \quad \text{(Equation 1)}$$

The minimum inhibitory concentration (MIC) of Substrate Compound 2 was determined as the range of Substrate Compound 2 concentrations over which the normalized bacteria density transitioned from zero to greater than zero.

Example 10

Conjugated Compound 4—In Vitro Bacterial Detection Efficacy

This EXAMPLE demonstrates the ability of the β-lactamase substrate-polymer conjugate to detect β-lactamase-producing bacteria. The inventors incubated Conjugated Compound 4 at various concentrations with four bacteria strains. Pseudomonas aeruginosa, Enterobacter cloacae, and Bacillus cereus are strains known to produce β-lactamases, while Escherichia coli DH5-α is a non-pathogenic bacteria commonly used as a non-β-lactamase-producing control bacteria. The conjugate changes color when incubated with β-lactamase-producing bacteria, even at low concentrations of the conjugate (as low as 280 μg/mL, which equals approximately forty-seven μg/mL of the β-lactamase substrate). Escherichia coli did not cause a color change.

Bacillus cereus, Enterobacter cloacae, and Pseudomonas aeruginosa were grown overnight in 1× tryptic soy broth, then diluted 1:1000 and grown to the mid-logarithmic growth phase.

Conjugated Compound 4 was dissolved in 1× phosphate-buffered saline at 9 mg/mL then serially diluted 1:2 in 50 μL of phosphate-buffered saline in a 96-well plate. 50 μL of bacteria in 1× tryptic soy broth was added to each well to a final concentration of $10^7$ CFU/mL The final solutions were 50% tryptic soy broth in phosphate-buffered saline and incubated shaking (100 rpm) at 37° C. for eighteen hours before images of the wells were taken.

At 4.5 mg/mL of Conjugated Compound 4 incubated with Bacillus cereus (a gram-positive bacteria), there seems to be an inhibition of bacterial growth and thus no color change from clear to bright yellow. At this concentration of conjugate, the equivalent concentration of Substrate Compound 2, 750 μg/mL, is higher than the concentrations tested in the microdilution assay (up to 200 μg/mL).

This EXAMPLE demonstrates a PEG hydrogel formulation with Compound 3 covalently attached to the backbone as an example of a diagnostic biomaterial. Compound 3 was mixed with 4-arm-PEG-thiol (20 kDa) at a 1:4 maleimide:thiol ratio to decorate one of the polymer's arms with the β-lactamase substrate. See, FIG. 8. Then the hydrogel was formed by adding crosslinker maleimide-PEG-maleimide (2 kDa) at a 1:1 maleimide:thiol ratio. Control non-β-lactamase-responsive hydrogels were formed similarly but without conjugating 3. After deprotection of the methoxybenzyl group and extensive hydrogel rinsing to remove any unbound 3 or organic solvents, both types of hydrogels were exposed to 1× phosphate-buffered saline or β-lactamase from Bacillus cereus. Only the responsive PEG hydrogels incubated in β-lactamase changed color, indicating the selective color change of the β-lactam compound in the presence of β-lactamase.

LIST OF EMBODIMENTS

Specific compositions of chromogenic β-lactamase substrate and methods of use have been disclosed. Those skilled in the chemical art will know that many more modifications besides those already described are possible without departing from the inventive concepts herein. The invention described in this specification is not to be restricted except in the spirit of the disclosure.

All patents and publications mentioned in this specification are expressly incorporated herein by reference to disclose and describe their methods and materials in connection with which the publications are cited. Nothing herein should be construed as an admission that the present invention does not antedate such publication by a prior invention. All statements as to the date or representation as to the contents of these documents are based on the information available to the applicants and constitute no admission as to the correctness of the dates or contents of these documents. If a conflict in definition occurs, the definitions of the present specification and claims control.

The invention is not limited to the particular embodiments described, and as such may vary. The terminology used to describe particular embodiments is not intended to be limiting. The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the chemical art will recognize. For example, while method steps or functions are presented in an order, alternative embodiments may perform functions in a different order, or functions may be performed substantially concurrently. The teachings of the disclosure provided can be applied to other methods. The embodiments described can be combined to provide further embodiments. Aspects of the disclosure can be modified to employ the compositions, functions, and concepts of the above references and application to provide yet further embodiments of the disclosure. Due to biological functional equivalency considerations, some changes can be made in a protein structure without affecting the biological or chemical action in kind or amount. These and other changes can be made to the disclosure, given the detailed description. All such modifications are included within the scope of the appended claims.

Specific elements of any of the embodiments can be combined or substituted for elements in other embodiments. While advantages associated with certain embodiments of the disclosure have been described in the context of these embodiments, other embodiments may also exhibit such advantages, and not all embodiments need exhibit such advantages to fall within the scope of the disclosure.

The technology described is further illustrated by these examples, which in no way should be construed as being further limiting.

When a range of values is provided, each intervening value, to the tenth of the unit of the lower limit, unless the context clearly dictates otherwise, between the upper and lower limit of that range and any other stated or intervening value in that range of values.

Some embodiments of the technology described can be defined according to the following numbered paragraphs:

A molecule containing a β-lactam ring, wherein the molecule comprises (a) a primary amine, (b) a protected carboxylic acid group, and (c) a 4-nitrobenzenethiol leaving group.

The β-lactam molecule, wherein the molecule has a chemical formula selected from the group consisting of:

Compound 1

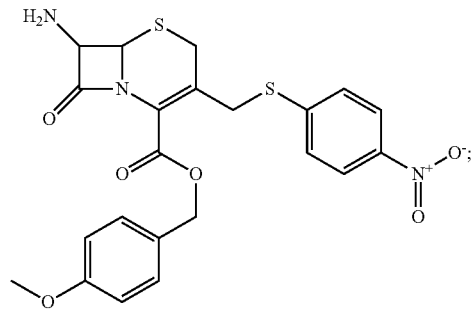

(Protected ANT)

Substrate Compound 2

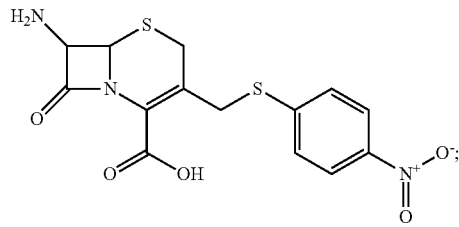

(ANT)

Compound 3

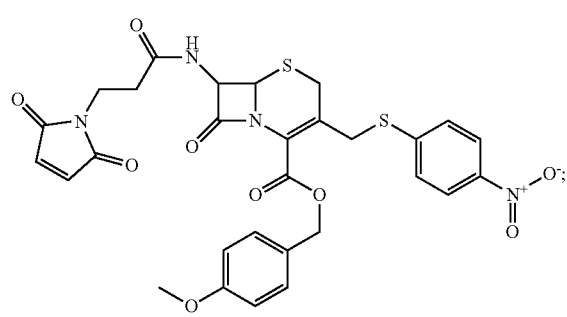

(ANT-maleimide)

Conjugated Compound 4

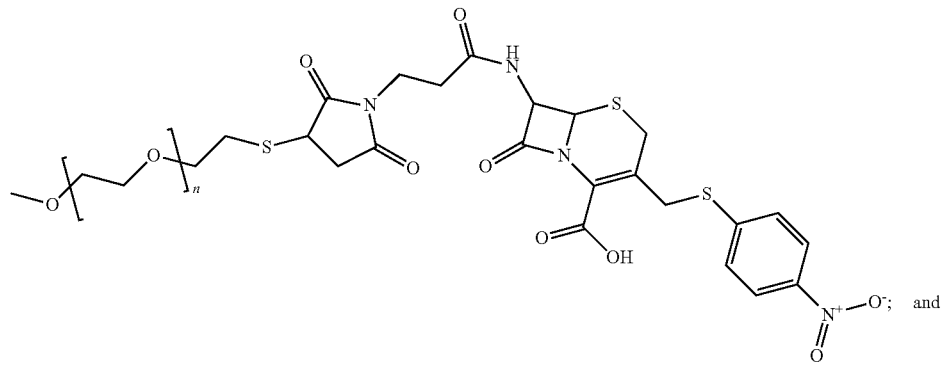

and

Conjugated Compound 5

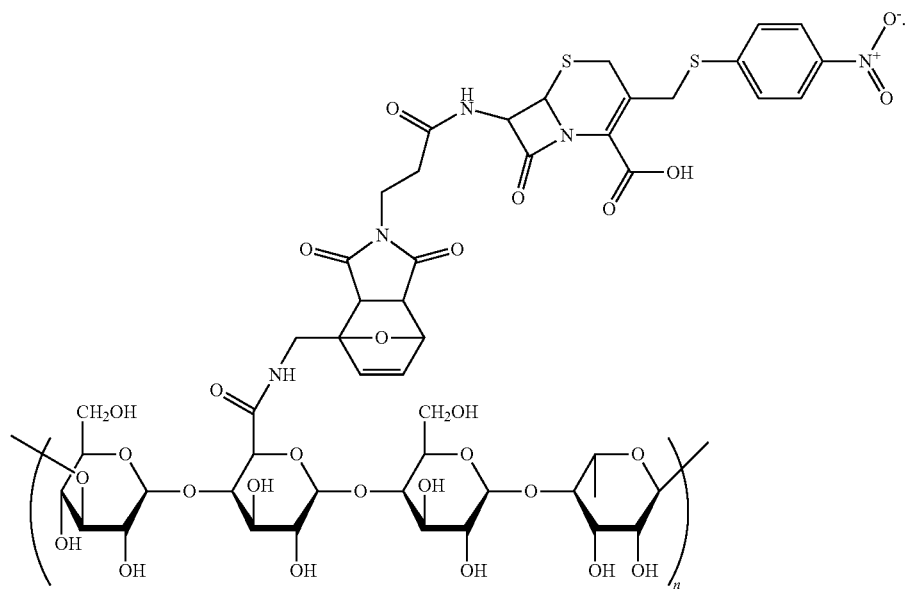

The β-lactam molecule, wherein the molecule is conjugated to another molecule.

The β-lactam molecule, wherein the molecule is conjugated to a macromolecule.

The β-lactam macromolecule, wherein the macromolecule is selected from the group consisting of gellan, polyethylene glycol (PEG), hyaluronic acid and alginate.

A formulation containing a β-lactam molecule selected from the group consisting of:

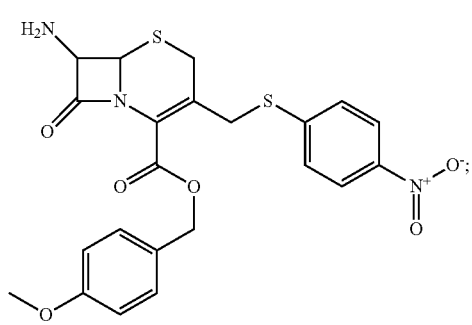

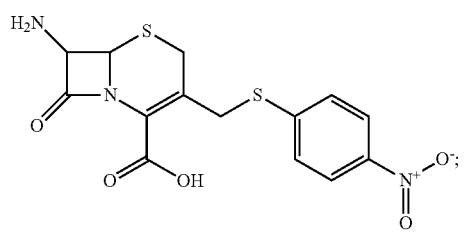

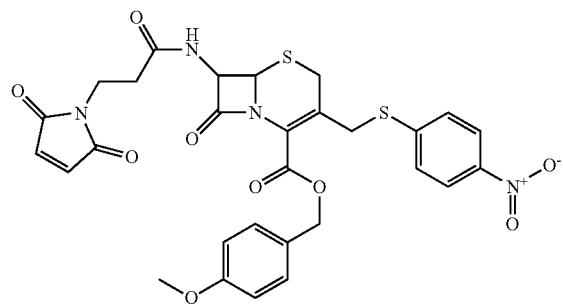
3
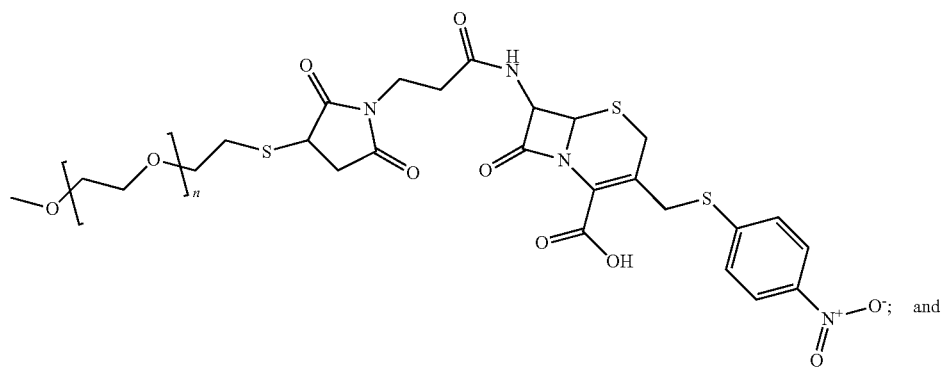
4
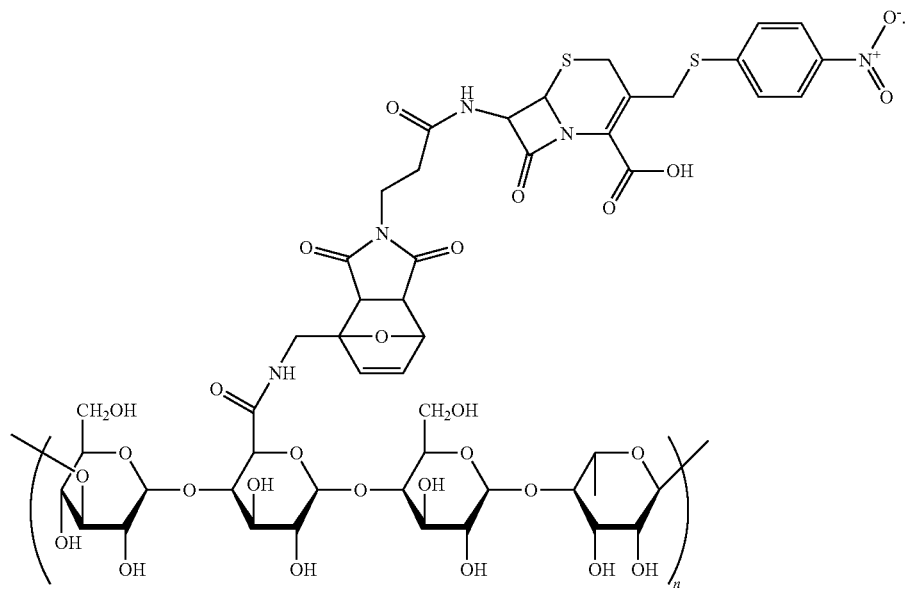

The formulation, wherein the formulation comprises a hydrogel for a wound dressing.

A method for synthesizing a molecule having the chemical formula:

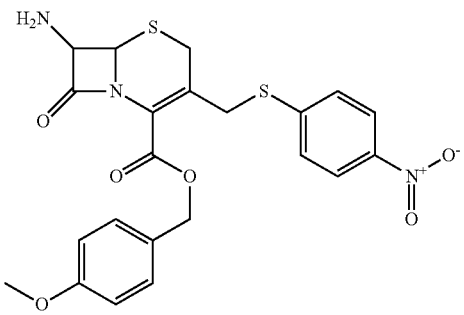 [SMILES: COc1ccc(COC(=O)C2=C(CSc3ccc([N+](=O)[O-])cc3)CSC3C(N)C(=O)N23)cc1]

comprising the step of combining ACLE with NBT in the presence of triethylamine 4-methylmorpholine.

The method of synthesis of Compound 1, further comprising the step of performing liquid chromatography/mass spectroscopy (LC-MS) analysis on the product of, wherein the results of the LC-MS analysis indicates the synthesis of Compound 1.

A method for synthesizing a molecule having the chemical formula:

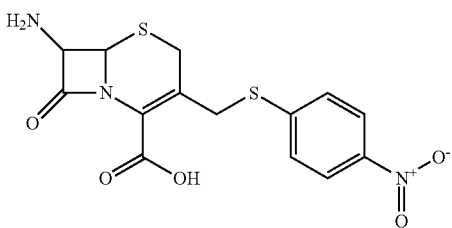

comprising the steps of:
(a) adding Compound 1 to dichloromethane;
(b) adding anisole to the mixture of step (a);
(c) adding trifluoroacetic acid to the mixture of step (b); and
(d) incubating on ice.

The method of synthesis of Substrate Compound 2, further comprising the step of performing nuclear magnetic resonance (NMR) analysis on the product of the synthesis, wherein the results of the NMR analysis indicates the synthesis of Substrate Compound 2.

A method for synthesizing a molecule having the chemical formula:

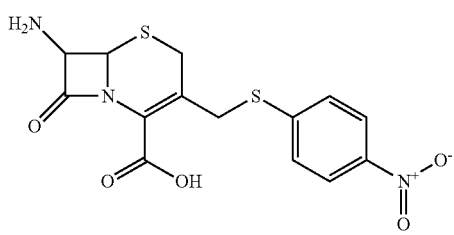

comprising the steps of combining ACLE with NBT in the presence of triethylamine 4-methylmorpholine, then:
(a) adding Compound 1 to dichloromethane;
(b) adding anisole to the mixture of step (a);
(c) adding trifluoroacetic acid to the mixture of step (b); and
(d) incubating on ice.

A method for synthesizing a molecule having the chemical formula:

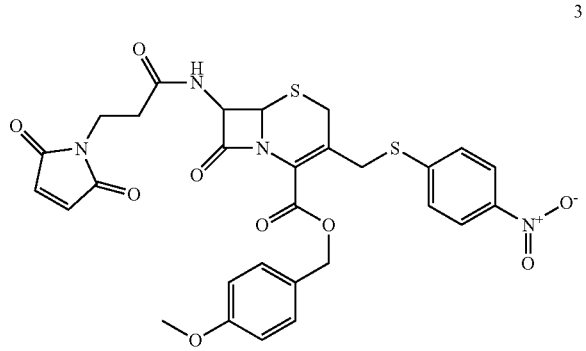 [SMILES: COc1ccc(COC(=O)C2=C(CSc3ccc([N+](=O)[O-])cc3)CSC3C(NC(=O)CCN4C(=O)C=CC4=O)C(=O)N23)cc1]

comprising the steps of:
(a) adding Compound 1 to maleimide;
(b) dissolving the combination of step (a) in dimethylformamide; and
(c) adding hexafluorophosphate azabenzotriazole tetramethyl uronium (HATU).

The method of synthesis of Compound 3, further comprising the step of performing nuclear magnetic resonance (NMR) analysis on the product of the synthesis, wherein the results of the NMR analysis indicates the synthesis of Compound 3.

A method for synthesizing a molecule having the chemical formula:

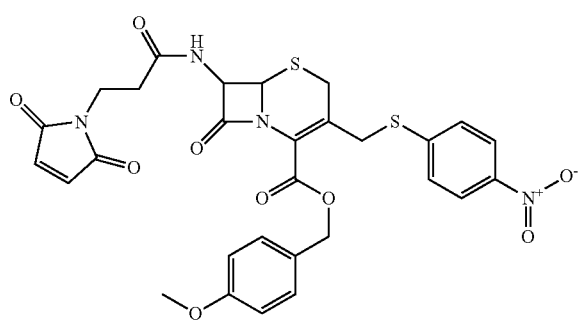

comprising the steps of combining ACLE with NBT in the presence of triethylamine 4-methylmorpholine, then:
(a) adding Compound 1 to maleimide;
(b) dissolving the combination of step (a) in dimethylformamide; and
(c) adding hexafluorophosphate azabenzotriazole tetramethyl uronium (HATU).

A method for synthesizing a molecule having the chemical formula:

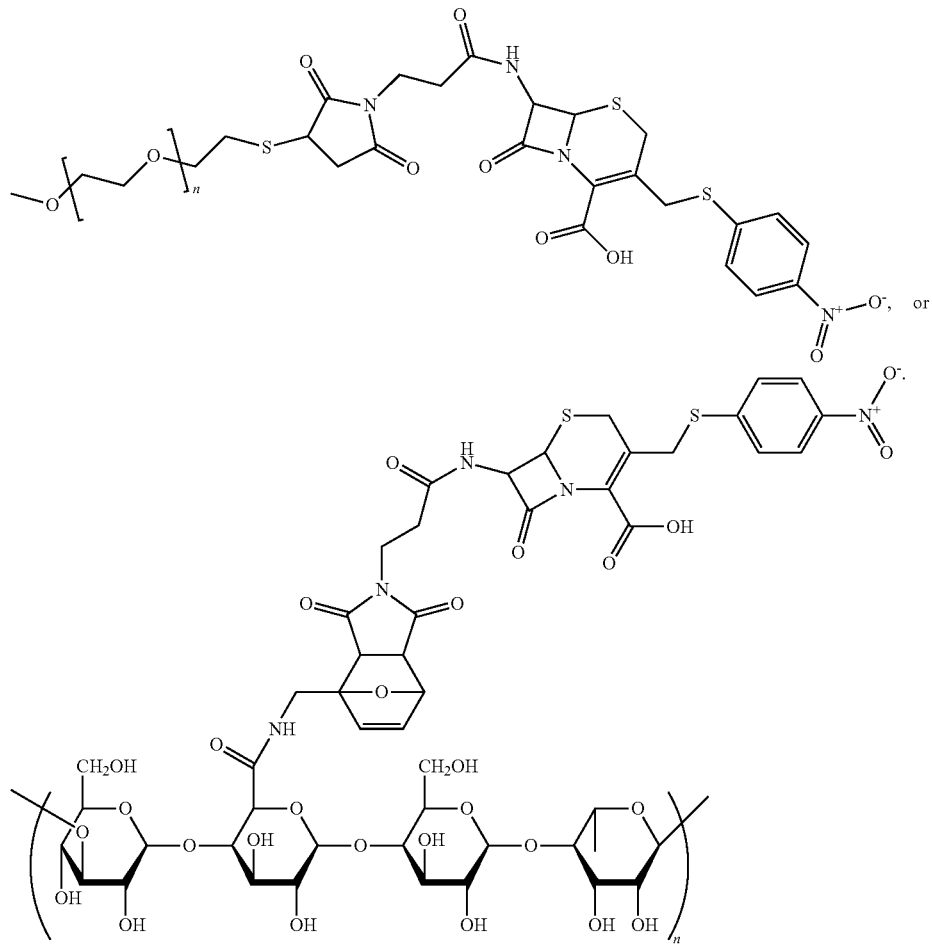

4 comprising the step of conjugating Compound 3 to a macromolecule by a Michael-type addition.

The method of synthesis of Conjugated Compound 4, further comprising the step of performing nuclear magnetic resonance (NMR) analysis on the product of the synthesis, wherein the results of the NMR analysis indicates the synthesis of Conjugated Compound 4.

A method for synthesizing a molecule having the chemical formula:

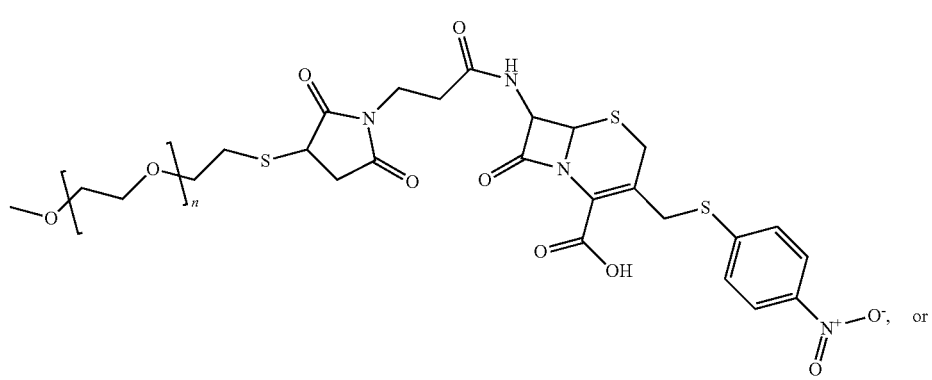

4

-continued

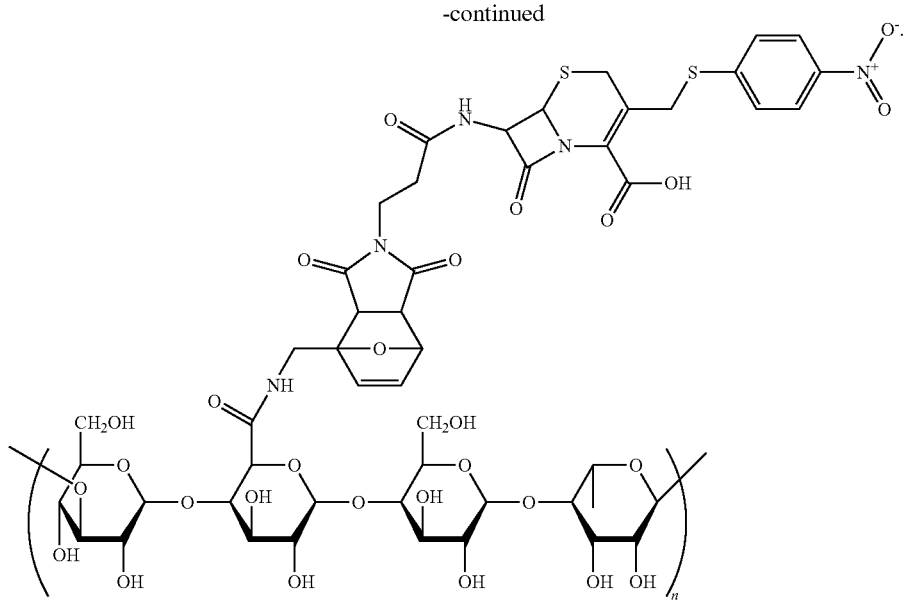

25 comprising the steps of combining ACLE with NBT in the presence of triethylamine 4-methylmorpholine, then:
(a) adding Compound 1 to maleimide;
(b) dissolving the combination of step (a) in THF; and
(c) adding hexafluorophosphate azabenzotriazole tetramethyl uronium (HATU), and then comprising the step of conjugating the product of step (c) to a macromolecule by a Michael-type addition.

A method for measuring the cleavage by a β-lactamase of a molecule containing a β-lactam ring, wherein the molecule comprises a primary amine; a protected carboxylic acid group, and a 4-nitrobenzenethiol leaving group, comprising the steps of (1) providing a sample of the molecule in a buffer; (2) measuring color of the sample of the molecule; (3) adding a β-lactamase to the sample of the molecule; (4) measuring the color change to the sample of the molecule following the addition of the β-lactamase; wherein a color change indicates the cleavage of the β-lactam ring in the molecule.

The method of measurement, wherein the molecule has a chemical formula selected from the group consisting of:

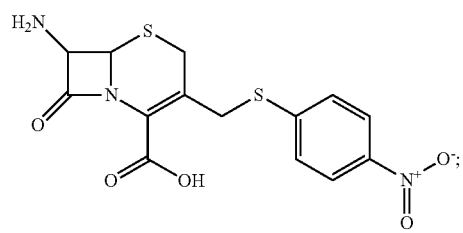

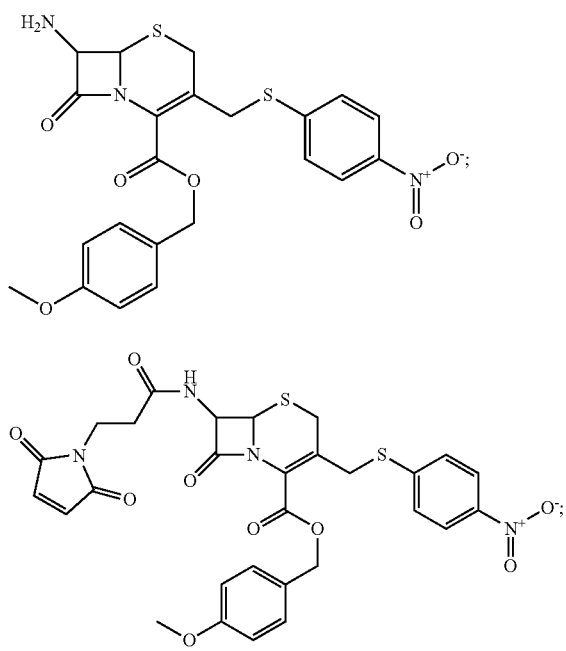

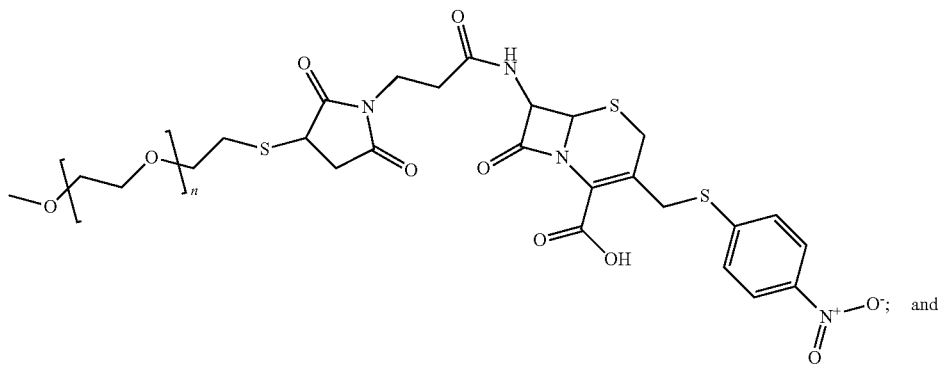

4

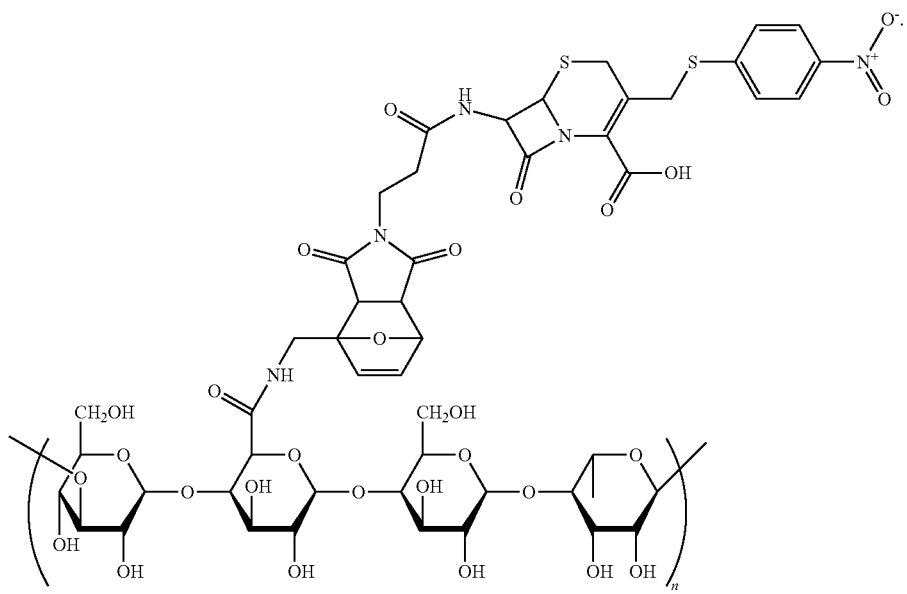

4

The method of measurement, wherein the color change measured is a decrease in the peak at 260 nm.

The method of measurement, wherein the color change comes with a shift in the molecule's absorbance spectrum.

The method of measurement, wherein the shift in the absorbance spectrum is a shift in the maximum absorbance peak shifts from 345 nm to 410 nm.

The method of measurement, wherein, (1) providing a second sample of the molecule in a buffer, wherein the second sample is a control sample; (2) measuring color of the second sample; wherein a color change in the sample to which the β-lactamase has been added relative to the color of the second sample indicates the cleavage of the β-lactam ring in the molecule in the sample to which the β-lactamase has been added.

The method of measurement, wherein the β-lactamase is a penicillinase or a cephalosporinase. The method of measurement, wherein the β-lactamase is an IL or a metallo-β-lactamase.

The method of measurement, wherein the buffer is a phosphate buffered saline (PBS).

A kit, comprising a detectable β-lactamase substrate (e.g., Substrate Compound 2), further comprising a lysis reagent, an agent that promotes the stabilization of the lysis reagent, and an agent that enhances the lysis of a bacterial cell by a lysis reagent (e.g., a metal chelator such as EDTA or EGTA).

The kit, wherein the lysis reagent lyses the bacterial cells but does not interfere with either the hydrolysis of the β-lactamase substrate.

The kit, wherein the lysis reagent is a detergent, such as mild non-denaturing detergent (e.g., Triton® X-100 or CHAPS).

The kit, wherein the lysis reagent is an enzyme or another agent that promotes the lysis of a bacterial cell.

The kit, wherein the agent that promotes the stabilization of the lysis reagent is thermal stable.

The kit, wherein the components are in a liquid composition; an agar plate; a paper strip; a paper disk; a tablet, in wells of a plate (e.g., a microtiter plate), tray, or cassette; in one or more tubes, (e.g., a test tube or Eppendorf tube), an array of tubes, a cassette or a panel, on or in a solid support, such as a paper strip, a paper disk.

The kit, wherein the components are dried and present in the wells of a well, tube, or panel.

The kit, wherein the components further comprise one or more of an AmpC inhibitor; a serine β-lactamase inhibitor in an amount sufficient to inhibit an extended-spectrum β-lactamases (ESBL) and an "older-spectrum" β-lactamase ("OSBL," e.g., TEM-1, SHV-1, or OXA-1), but not a class A serine carbapenemase; a metal chelator; and another extended-spectrum β-lactamases (ESBL) inhibitor.

From described embodiments described in this specification, other embodiments will be evident to those of ordinary skill in the chemical art. The detailed description is illustrative and not restrictive. This invention is not limited to the particular embodiments, methodology, protocols, and reagents described in this specification and as such can vary. The scope of the invention is defined solely by the appended claims.

We claim:

1. A diagnostic agent that changes color in response to presence of beta lactamases, wherein the diagnostic agent consists of the following formula:

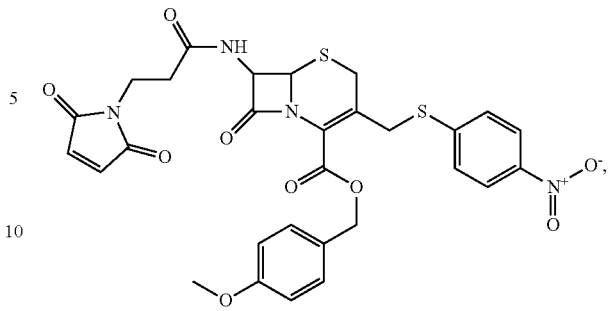

wherein the maleimide moiety in the structure above facilitates conjugation to a hydrogel forming polymer; further wherein the polymer is not an oligosaccharide; and wherein the diagnostic color change response is from clear to yellow when the B-lactam ring is hydrolyzed, expelling the 4-nitrobenzenethiol leaving group.

2. A formulation comprising the molecule of claim 1, wherein the formulation comprises a hydrogel in a wound dressing.

3. The molecule of claim 1, wherein the polymer is selected from the group consisting of gellan, polyethylene glycol (PEG), hyaluronic acid, and alginate.

* * * * *